US012697370B2

(12) United States Patent
Moore et al.

(10) Patent No.: US 12,697,370 B2
(45) Date of Patent: Aug. 4, 2026

(54) PSG1 FOR USE IN THE TREATMENT OF OSTEOARTHRITIS

(71) Applicant: UNIVERSITY COLLEGE CORK—NATIONAL UNIVERSITY OF IRELAND, CORK, Cork (IE)

(72) Inventors: Tom Moore, Cork (IE); Anthony James Peterson Clover, Cork (IE)

(73) Assignee: UNIVERSITY COLLEGE CORK—NATIONAL UNIVERSITY OF IRELAND, CORK, Cork (IE)

( * ) Notice: Subject to any disclaimer, the term of this patent is extended or adjusted under 35 U.S.C. 154(b) by 470 days.

(21) Appl. No.: 18/555,431

(22) PCT Filed: Apr. 14, 2022

(86) PCT No.: PCT/EP2022/060148
§ 371 (c)(1),
(2) Date: Oct. 13, 2023

(87) PCT Pub. No.: WO2022/219168
PCT Pub. Date: Oct. 20, 2022

(65) Prior Publication Data
US 2024/0197827 A1 Jun. 20, 2024

(30) Foreign Application Priority Data

Apr. 14, 2021 (EP) ..................................... 21168470

(51) Int. Cl.
*A61K 38/17* (2006.01)
*A61K 9/00* (2006.01)
*A61P 19/02* (2006.01)
*C07K 16/30* (2006.01)

(52) U.S. Cl.
CPC ........ *A61K 38/1774* (2013.01); *A61K 9/0019* (2013.01); *A61P 19/02* (2018.01); *C07K 16/3092* (2013.01)

(58) Field of Classification Search
None
See application file for complete search history.

(56) References Cited

U.S. PATENT DOCUMENTS

2006/0063162 A1 3/2006 Deng

FOREIGN PATENT DOCUMENTS

WO 2017049082 A2 3/2017

OTHER PUBLICATIONS

Tom Moore et al, "Pregnancy-specific glycoproteins: complex gene families regulating maternal-fetal interactions", International Journal of Developmental Biology., vol. 58, No. 2-3-4, Jan. 1, 2014 (Jan. 1, 2014), pp. 273-280.
Angela Ballesteros et al, "Induction and Activation of Latent Transforming Growth Factor-[beta] 1 Are Carried out by Two Distinct Domains of Pregnancy-specific Glycoprotein 1 (PSG1)", Journal of Biological Chemistry, vol. 290, No. 7, Dec. 29, 2014 (Dec. 29, 2014), pp. 4422-4431.
Karlie Jones et al, "Recombinant Pregnancy Specific Glycoprotein 1 has a protective role In a Murine Model of Acute Graft Versus Host Disease", Biology of Blood and Marrow Transplantation, Sep. 1, 2018 (Sep. 1, 2018).
S M Blois et al, "Pregnancy-specific glycoprotein 1 (PSG1) activates TGF-[beta] and prevents dextran sodium sulfate (DSS)-induced colitis in mice", Mucosal Immunology,vol. 7, No. 2, Aug. 14, 2013 (Aug. 14, 2013), pp. 348-358.
Testa Gianluca et al, "Intra-Articular Injections in Knee Osteoarthritis: A Review of Literature", Journal of Functional Morphology and Kinesiology, vol. 6, No. 1, Feb. 3, 2021 (Feb. 3, 2021), p. 15.
International Search Report—Partial for Int'l Appl. No. PCT/EP2022/060148, entitled PSG1 for Use in the Treatment of Osteoarthritis, consisting of 5 pages. Date Mailed: Sep. 15, 2022.

*Primary Examiner* — Oluwatosin A Ogunbiyi
(74) *Attorney, Agent, or Firm* — HAMILTON, BROOK, SMITH & REYNOLDS, PC

(57) ABSTRACT

The use of Fc-tagged Pregnancy-specific glycoprotein 1 (PSG1-Fc) in a method of treatment of osteoarthritis or damaged cartilage in a human, in which the PSG1 is administered by intra-articular injection, is described. Also described is the use of CC49 in a method of treatment of osteoarthritis or damaged cartilage in an equine mammal, in which the CC49 is administered by intra-articular injection. (FIG. 3A-C) Also described is the use of PSG1 in a method of treatment of wounds, scarring, burns and diabetic ulcers in a mammal.

6 Claims, 6 Drawing Sheets

Specification includes a Sequence Listing.

| Upregulated genes (Replicate 1) | Fold change | Upregulated genes (Replicate 2) | Fold change |
|---|---|---|---|
| CXCL5 | 27.21 | TNF | 11.05 |
| CXCL11 | 22.88 | CXCL5 | 10.15 |
| CCL7 | 21.74 | CXCL11 | 9.13 |
| CCL2 | 10.65 | CCL2 | 6.92 |
| CXCL2 | 6.07 | MMP9 | 6.88 |
| MMP7 | 4.61 | CXCL1 | 4.15 |
| MMP9 | 4.58 | FGF7 | 4.14 |
| IL6 | 4.01 | MMP7 | 3.46 |
| MMP1 | 3.76 | CCL7 | 3.42 |
| ITGB3 | 2.16 | CXCL2 | 3.24 |

PSG1 FOR USE IN THE TREATMENT OF OSTEOARTHRITIS

This application is the U.S. National Stage of International Application No. PCT/EP2022/060148, filed Apr. 14, 2022, which designates the U.S., published in English, and claims priority under 35 U.S.C. § 119 or 365(c) to European Application No. 21168470.9, filed Apr. 14, 2021. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 6226.1001-002 Seq. listing.txt; created Oct. 12, 2023, 12,651 Bytes in size.

FIELD OF THE INVENTION

The present invention relates to the use of placenta expressed proteins to treat disease.

BACKGROUND TO THE INVENTION

Pregnancy-specific glycoproteins (PSG) are considered to be involved in the regulation of immune, angiogenic and platelet responses at the maternal-fetal interface and in the maternal circulation during pregnancy. PSG proteins are part of the carcinoembryonic antigen cell adhesion molecule (CEACAM) family, which by itself is a member of the immunoglobulin superfamily. PSG proteins differ considerably in structure between primates, equids and rodents, but retain conserved functions (Aleksic D, et al. Convergent evolution of pregnancy-specific glycoproteins in human and horse. Reproduction. 2016 September; 152(3):171-84. doi: 10.1530/REP-16-0236. Epub 2016 Jun. 8. Moore T, Dveksler G S. Pregnancy-specific glycoproteins: complex gene families regulating maternal-fetal interactions. Int J Dev Biol. 2014; 58(2-4):273-80. doi: 10.1387/ijdb.130329gd. Review. PMID:25023693.). There are 11 and 17 different PSG genes encoding PSG proteins in humans and mice respectively. Human PSGs are composed of one N-terminal immunoglobulin variable (IgV)-like domain (N domain) followed by generally two to three Ig constant (IgC)-like domains of two different types (named A and B), whereas rodent PSGs contain two to nine consecutive N domains followed by one IgC-like domain. The 7 equine CEACAM-derived PSG-like proteins have single N and A2 domains (Aleksic et al., 2016).

PSG1 is an abundantly expressed member of the 11 different human PSG genes, and, in one study, total PSG protein concentration was estimated to be greater than 100 µg/ml in the third trimester of pregnancy. During pregnancy, transforming growth factor beta (TGF-β) regulates trophoblast invasion, angiogenesis and extracellular matrix production. Treatment of different cells with PSG1 or other PSGs increased the secretion of total TGF-β1 in the supernatant as determined by ELISA and also the activation of latent TGF-β1 [Ballesteros A, Mentink-Kane M M, Warren J, Kaplan G G, Dveksler G S.

Induction and activation of latent transforming growth factor-β1 are carried out by two distinct domains of pregnancy-specific glycoprotein 1 (PSG1).

J Biol Chem. 2015 Feb. 13; 290(7):4422-31. doi: 10.1074/jbc.M114.597518. Epub 2014 Dec. 29.].

WO2017049082 describes one specific PSG protein, PSG1, and its involvement in pathways devoted to induction of immune tolerance. PSG1 is involved in activation of transforming growth factor-β 1 (TGFβ1), a cytokine essential to suppression of inflammatory T-cells and important for differentiation of tolerance inducing CD4+CD25+FoxP3+ regulatory T cells (Tregs), a cell population shown to be important in the prevention of Graft versus Host Disease (GvDH).

Jones et al. (Biology of Blood and Marrow Transplantation, 1 Sep. 2018) describes the protective role played by recombinant PSG1 in a murine model of acute graft versus host disease).

Blois et al. (Mucosal Immunology, Vol. 7, No. 2, 14 Aug. 2013) describes the use of PSG1 in the prevention of DSS-induced colitis in mice.

SUMMARY OF THE INVENTION

In one aspect, the invention provides a Pregnancy-specific glycoprotein (for example PSG1) for use in a method of treating or preventing a condition characterised by loss of, or damage to, cartilage. In one embodiment, the condition is a degenerative joint condition. In one embodiment, the degenerative joint condition is osteoarthritis. In another embodiment, the condition is damaged cartilage caused by trauma (for example, a fall or sports injury). In one embodiment, the PSG1 is administered by intra-articular injection. In one embodiment, the method is a method of slowing, halting, or reversing the loss of cartilage in the affected joint. In one embodiment, the method is for treating osteoarthritis in the knee, hip or hand. In one embodiment, the treatment is a causal treatment. In another embodiment, the treatment is a symptomatic treatment, for example a method of treating a symptom of osteoarthritis such as joint pain or stiffness. In one embodiment, the method is a method of repairing damaged cartilage in a subject. FIGS. 3A-C demonstrate the effective treatment of osteoarthritis using PSG1-Fc and CC49-Fc.

According to another aspect of the present invention, there is provided a Pregnancy-specific glycoprotein, for example Pregnancy-specific glycoprotein 1 (PSG1), for use in a method of treating a wound in a mammal. The PSG1 has been shown in mouse and pig animal models to promote wound contracture or re-epithelialisation of the wound and accelerate wound closure compared with an untreated wound.

Typically, the method of the invention is for accelerating closure of the wound compared with an untreated wound.

Typically, the wound is a cutaneous wound. However, the invention also applies to treatment of non-cutaneous wounds, for example wounds to organs other than the skin. Such wounds can be caused by, for example, surgery, trauma, drug use or disease. In one embodiment, the wound is a diabetic ulcer, for example a diabetic food ulcer.

Typically, the PSG1 is administered topically to the wound. Typically, the method comprises applying a PSG1 topical formulation to the wound, especially the periphery of the wound.

In any embodiment, the PSG1 may be administered subcutaneously to the wound, typically by subcutaneous injection.

The PSG1 is typically administered in an amount effective to promote epithelialisation by keratinocytes at the site of the cutaneous wound.

In any embodiment, the wound comprises a scar. In any embodiment, the PSG1 is administered to the scar.

In any embodiment, the wound is a wound generated as a result of excision of a hypertrophic scar.

In any embodiment, the wound comprises or consists of a keloid scar.

According to another aspect of the present invention, there is provided a Pregnancy-specific glycoprotein, for example Pregnancy-specific glycoprotein 1 (PSG1), for use in a method of treating a keloid scar in a mammal.

According to another aspect of the present invention, there is provided a Pregnancy-specific glycoprotein, for example Pregnancy-specific glycoprotein 1 (PSG1), for use in a method of treating or preventing hypertrophic scarring in a mammal. In any embodiment, the method comprises excising a hypertrophic scar and then administering the Pregnancy-specific glycoprotein to the wound generated by excision of the scar.

In a further aspect, the invention provides Fc-tagged Pregnancy-specific glycoprotein 1 (PSG1-Fc) for use in a method of treating a wound in a mammal, especially a cutaneous wound. In one embodiment, the PSG1-Fc is administered to the wound topically or by intradermal (IV) administration.

In a further aspect, the invention provides a PSG1 topical formulation, comprising a therapeutically effective amount of Pregnancy-specific glycoprotein 1 (PSG1) in combination with a pharmaceutically acceptable excipient. The PSG1 topical formulation may be a cream, ointment, gel, oil suspension or lotion.

In a further aspect, the invention provides Fc-tagged Pregnancy-specific glycoprotein 1 (PSG1-Fc) for use as a medicament.

In one embodiment, the PSG1 is administered by subcutaneous, intradermal, intravenous, or intraperitoneal delivery, or by injection to the affected area. In one embodiment, the PSG1 is administered by intra-articular injection.

In any embodiment, the PSG1 is administered to the mammal by transfecting the mammal with a PSG1 (or PSG1-Fc) expression vector.

In any embodiment, the PSG1 is administered to the mammal by administering cells to the mammal that have been transfected with a PSG1 (or PSG1-Fc) expression vector. In any embodiment, the PSG1 is administered to the mammal by administering cells to the mammal that have been pre-treated with a PSG1 (for example cells that have been incubated with or cultured in the presence of PSG1). In any embodiment, the PSG1 and cells (for example, mesenchymal stem cells) are co-administered to the mammal. In any embodiment, the cells are stem cells. In any embodiment, the cells are mesenchymal stem cells. In any embodiment, the donor cells are obtained from the recipient. In one embodiment, the donor cells are obtained from a mammal of the same species (e.g. human to human or horse to horse) (allogenic cell therapy). In any embodiment, the cells are transfected ex-vivo.

The methods of the invention provided above recite PSG1, and modified versions of PSG1 such as PSG1-Fc, in therapy. However, the invention also relates to the use of PSG proteins other than PSG1 (and modified versions thereof) in the therapeutic methods described above.

In any embodiment, the PSG1 (or PSG) is modified with a functional moiety. The functional moiety may be configured to increase the plasma half-life of the modified PSG1. The functional moiety may be configured to increase the cell permeation functionality of the modified PSG1. The functional moiety may be configured to increase the activity of the modified PSG1. The functional moiety may be configured to facilitate the purification of the modified PSG1.

Examples of modification of PSG1 polypeptides are provided below, and include addition of an antibody fragment, for example an Fc moiety, addition of a PEG functional group, replacement of a natural amino acid with a L-isomer. In one embodiment, the functional group is an Fc moiety. In one embodiment, the Fc moiety is modified to have an increased plasma half-life compared with a native Fc moiety. Modified Fc tags are described in the following papers: Algirdas Grevys, Malin Bern, Stian Foss, Diane Bryant, Terje Bratlie, Anders Moen, Kristin Støen Gunnarsen, Audun Aase, Terje Einar Michaelsen, Inger Sandlie and Jan Andersen. Fc Engineering of Human IgG1 for Altered Binding to the Neonatal Fc Receptor Affects Fc Effec-tor Functions. Journal of Immunology Jun. 1, 2015, 194 (11) 5497-5508. Dall'Acqua W F, Kiener P A, Wu H. Properties of human IgG1 s engineered for enhanced binding to the neonatal Fc receptor (FcRn). The Journal of Biological Chemistry. 281:23514-23524 (2006). (2006). Abhishek Saxena and Donghui Wu. Advances in Therapeutic Fc Engineering—Modulation of IgG-Associated Effector Functions and Serum Half-life. Frontiers in Immunology. 2016; 7: 580. Exemplary modifications to human Fc tags include the triple substitution YTE (M252Y/S254T/T256E) in the CH2 domain and (H433K/N434F) in the CH3 domain to increase stability and half-life (SEQUENCE ID NO: 3). These modifications may be performed using site directed mutagenesis. In one embodiment, the invention provides a PSG1 protein conjugated with an Fc tag encoded by SEQUENCE ID NO: 3.

In another aspect, the invention provides CC49 (typically recombinant CC49), for use in a method of treating a wound in a mammal, typically a non-human mammal. In a preferred embodiment, the mammal is equine (i.e. a horse). Data provided herein shows that CC49 exhibits a range of gene regulatory activities consistent with tissue repair actions similar to PSG1. For example, CC49, similar to PSG1, regulates cytokine expression in human cell lines (HaCaT, Jurkat) representing keratinocyte and lymphocyte lineages, respectively. CC49 enhances HaCaT and mesenchymal stem cell (MSC) migration in an in vitro scratch wound assay (FIG. 1A-C).

In another aspect, the invention provides CC49 (typically recombinant CC49), for use in a method of treating a condition in a mammal characterised by loss of, or damage to, cartilage. In a preferred embodiment, the mammal is equine (i.e. a horse). In any embodiment, the condition is a degenerative condition of the joints (for example, a joint disease such as osteoarthritis). In any embodiment, the condition is a traumatic injury to cartilage, for example caused by a fall or other type of trauma. In any embodiment, the condition causes lameness due to tissue damage in response to a stimulus (for example an injury). In any embodiment, the CC449 is administered by injection directly into the injured tissue or for intra-articular injection. In one particular aspect, the invention provides CC49, especially modified CC49 such as CC49-Fc, for use in a method of treatment or prevention of a joint condition in an equine mammal (typically osteoarthritis), in which the CC49 is administered to the equine mammal by intra-articular injection into the affected joint.

In any embodiment, the CC49 is modified with a functional group. In any embodiment, the functional group is configured to increase the plasma half-life of the modified CC49. In any embodiment, the functional group is an Fc moiety derived from equine IgG1 (an example is described in Wagner B1, Robeson J, McCracken M, Wattrang E, Antczak D F. Horse cytokine/IgG fusion proteins—mammalian expression of biologically active cytokines and a system to verify antibody specificity to equine cytokines. Vet Immunol Immunopathol. 2005 May 1; 105(1-2):1-14. DOI: 10.1016/j.vetimm.2004.11.010). The Fc tag is also useful for purifying the protein during pharmaceutical production.

In any embodiment, the CC49 is administered parentally. In any embodiment, the CC449 is administered by intra-articular injection.

In another aspect, the invention provides recombinant CC49 for use as a medicament.

In another aspect, the invention provides Fc-tagged CC49 (for example Fc labelled recombinant CC49).

In another aspect, the invention provides Fc-tagged CC49 for use as a medicament.

Other aspects and preferred embodiments of the invention are defined and described in the other claims set out below.

DETAILED DESCRIPTION OF THE INVENTION

Figure 1A:
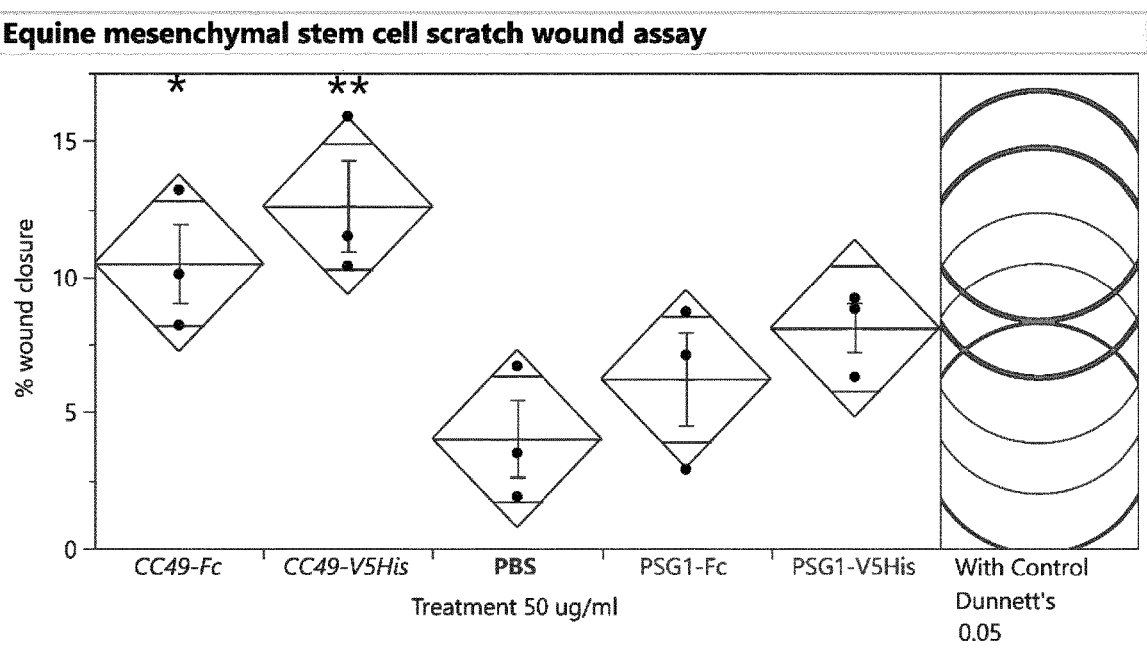
FIG. 1. PSG1 and CC49 proteins enhance wound closure in cell line scratch wound assays. A) PSG1-Fc, PSG1-V5His, CC49-Fc, CC49-V5His or 50 µl PBS treated equine MSC cells (n=3) after 16 hours. B) PSG1-Fc, PSG1-V5His, CC49-Fc, CC49-V5His or 50 µl PBS treated human MSCs (n=3) after 16 hours. C) PSG1-Fc, PSG1-V5His, CC49-Fc, CC49-V5His or 50 µl PBS treated HaCaT cells (n=3) after 16 hours. (*P<0.05, P<0.01, *P<0.001). D) PSG1-V5His or 50 µl PBS treated human HaCaT cells were analysed for gene expression changes using RT$^2$ Profiler™ PCR Array Human Wound Healing (330231, cat no. PAHS-121ZE-4; Qiagen, UK).

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, kiang and zebra.

As used herein, the term PSG protein refers to CEACAM-related proteins lacking a cell membrane anchor and predominantly expressed in placental tissues. Such proteins are found in a subset of mammals including, for example, primates, rodents, equids, bats, but not in, for example, ungulates and canids (Robert Kammerer, Wolfgang Zimmermann. Coevolution of activating and inhibitory receptors within mammalian carcinoembryonic antigen families. BMC Biol. 2010; 8: 12. Published online 2010 Feb. 4. doi: 10.1186/1741-7007-8-12). Examples of PSG gene and protein sequences are available (McLellan A S, Fischer B, Dveksler G, Hori T, Wynne F, Ball M, Okumura K, Moore T, Zimmermann W. Structure and evolution of the mouse pregnancy-specific glycoprotein (Psg) gene locus. BMC Genomics. 2005 Jan. 12; 6:4. PMID: 15647114; Kammerer & Zimmermann, 2010; Aleksic et al., 2016). Generally, the PSG (i.e. PSG1) is a recombinant protein.

As used herein, the term "Pregnancy-specific glycoprotein 1" or "PSG1" refers to the full-length protein represented by Sequence ID 1 below, which includes the signal sequence (amino acid residues 1-34), mature peptide (residues 35-419). The term also includes the mature peptide without the signal sequence.

```
SEQUENCE ID NO: 1:
PSG1
MGTLSAPPCT QRIKWKGLLL TASLLNFWNL PTTAQVTIEA

EPTKVSEGKD VLLLVHNLPQ NLTGYIWYKG QMRDLYHYIT

SYVVDGEIII YGPAYSGRET AYSNASLLIQ NVTREDAGSY

TLHIIKGDDG TRGVTGRFTF TLHLETPKPS ISSSNLNPRE

TMEAVSLTCD PETPDASYLW WMNGQSLPMT HSLKLSETNR

TLFLLGVTKY TAGPYECEIR NPVSASRSDP VTLNLLPKLP

KPYITINNLN PRENKDVLNF TCEPKSENYT YIWWLNGQSL

PVSPRVKRPI ENRILILPSV TRNETGPYQC EIRDRYGGIR

SDPVTLNVLY GPDLPRIYPS FTYYRSGEVL YLSCSADSNP

PAQYSWTINE KFQLPGQKLF IRHITTKHSG LYVCSVRNSA

TGKESSKSMT VEVSDWTVP
```

The term "PSG1" also includes Fc-tagged PSG1 proteins (PSG1-Fc), an example of which is provided in SEQUENCE ID NO: 2 below in which the Fc tag is modified by site directed mutagenesis to introduce MTS mutations M252Y/S254T/T256E and HN mutations H433K/N434F:

```
PSG1-Fc ORF
                                   SEQUENCE ID NO: 2
ATGGGAACCCTCTCAGCCCCTCCCTGCACACAGCGCATCAAATGGAAGGGGCTCCTG

CTCACAGCATCACTTTTAAACTTCTGGAACCTGCCCACCACTGCCCAAGTCACGATTG

AAGCCGAGCCAACCAAAGTTTCCGAGGGGAAGGATGTTCTTCTACTTGTCCACAATTT

GCCCCAGAATCTTACCGGCTACATCTGGTACAAAGGGCAAATGAGGGACCTCTACCA

TTACATTACATCATATGTAGTAGACGGTGAAATAATTATATATGGGCCTGCATATAGTG

GACGAGAAACAGCATATTCCAATGCATCCCTGCTGATCCAGAATGTCACCCGGGAGG

ACGCAGGATCCTACACCTTACACATCATAAAGGGAGATGATGGGACTAGAGGAGTAA

CTGGACGTTTCACCTTCACCTTACACCTGGAGACTCCTAAGCCCTCCATCTCCAGCAG

CAACTTAAATCCCAGGGAGACCATGGAGGCTGTGAGCTTAACCTGTGACCCTGAGAC

TCCAGACGCAAGCTACCTGTGGTGGATGAATGGTCAGAGCCTCCCTATGACTCACAG

CTTGAAGCTGTCCGAAACCAACAGGACCCTCTTTCTATTGGGTGTCACAAAGTATACT

GCAGGACCCTATGAATGTGAAATACGGAACCCAGTGAGTGCCAGCCGCAGTGACCCA

GTCACCCTGAATCTCCTCCCGAAGCTGCCCAAGCCCTACATCACCATCAACAACTTAA

ACCCCAGGGAGAATAAGGATGTCTTAAACTTCACCTGTGAACCTAAGAGTGAGAACTA

CACCTACATTTGGTGGCTAAATGGTCAGAGCCTCCCGGTCAGTCCCAGGGTAAAGCG

ACCCATTGAAAACAGGATCCTCATTCTACCCAGTGTCACGAGAAATGAAACAGGACCC

TATCAATGTGAAATACGGGACCGATATGGTGGCATCCGCAGTGACCCAGTCACCCTG

AATGTCCTCTATGGTCCAGACCTCCCCAGAATTTACCCTTCATTCACCTATTACCGTTC

AGGAGAAGTCCTCTACTTGTCCTGTTCTGCGGACTCTAACCCACCGGCACAGTATTCT

TGGACAATTAATGAAAAGTTTCAGCTACCAGGACAAAAGCTCTTTATCCGCCATATTAC

TACAAAGCATAGCGGGCTCTATGTTTGCTCTGTTCGTAACTCAGCCACTGGCAAGGAA

AGCTCCAAATCCATGACAGTCGAAGTCTCTGACTGGACAGTTCCCGAGCCCAAATCTT
```

-continued

```
GTGACAAAACTCACACATGCCCACCGTGCCCAGCACCTGAACTCCTGGGGGGACCGT

CAGTCTTCCTCTTCCCCCCAAAACCCAAGGACACCCTCTACATCACCCGGGAACCTGA

GGTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGGGAGGAGCAGT

ACAACAGCACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCT

TCTATCCCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTACAGCAAG

CTCACCGTGGACAAGAGCAGGTGGCAGCAGGGGAACGTCTTCTCATGCTCCGTGATG

CATGAGGCTCTGAAGTTCCACTACACGCAGAAGAGCCTCTCCCTGTCTCCGGGTAAA

TGA
```

SEQUENCE ID NO: 3 provides the open reading frame for the modified Fc tag that incorporates the MTS mutations M252Y/S254T/T256E and HN mutations H433K/N434F:

```
Modified human Fc ORF
                                  SEQUENCE ID NO: 3
GAGCCCAAATCTTGTGACAAAACTCACACATGCCCACCGTGCCCAGCAC

CTGAACTCCTGGGGGGACCGTCAGTCTTCCTCTTCCCCCCAAAACCCAA

GGACACCCTCTACATCACCCGGGAACCTGAGGTCACATGCGTGGTGGTG

GACGTGAGCCACGAAGACCCTGAGGTCAAGTTCAACTGGTACGTGGACG

GCGTGGAGGTGCATAATGCCAAGACAAAGCCGCGGGAGGAGCAGTACAA

CAGCACGTACCGTGTGGTCAGCGTCCTCACCGTCCTGCACCAGGACTGG

CTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACC

ACAGGTGTACACCCTGCCCCCATCCCGGGATGAGCTGACCAAGAACCAG

GTCAGCCTGACCTGCCTGGTCAAAGGCTTCTATCCCAGCGACATCGCCG

TGGAGTGGGAGAGCAATGGGCAGCCGGAGAACAACTACAAGACCACGCC

TCCCGTGCTGGACTCCGACGGCTCCTTCTTCCTCTACAGCAAGCTCACC
```

-continued

```
GTGGACAAGAGCAGGTGGCAGCAGGGGAACGTCTTCTCATGCTCCGTGA

TGCATGAGGCTCTGAAGTTCCACTACACGCAGAAGAGCCTCTCCCTGTC

TCCGGGTAAATGA
```

As used herein, the term "CC49" refers to the equine PSG-like CEACAM49 full-length protein represented by Sequence ID 4 below, which includes the signal sequence (amino acid residues (which is usually residues 1 to 32 or 38), mature peptide. The term also includes the mature peptide without the signal sequence.

```
SEQUENCE ID NO: 4:
CC49
MQSPSGPAHR GCVPWQALLL AVSILAFWNL PATVQFTIES

VPNNVTEGKD VLLLVHNLTG NILGYMWFKG NGARPHKQIK

FYDVDTKAFS TGPLATGRET MYPNGSLLFQ NVTTEYAGNY

TLLVLKRSLI YEVGTGQVHV YNPGSNTSIG ISVIHKDPSY

RA
```

The term "CC49" also includes Fc-tagged CC49 proteins (CC49-Fc), an example of which is provided in SEQUENCE ID NO: 5 below:

```
CC49-Fc ORF
                                  SEQUENCE ID NO: 5
ATGCAATCACCCTCAGGCCCTGCTCACAGAGGATGTGTCCCTTGGCAGGCGCTCCTC

TTGGCAGTCTCAATCTTAGCCTTCTGGAACCTGCCCGCCACTGTCCAGTTCACTATTG

AGTCGGTGCCGAACAATGTTACTGAAGGAAAGGATGTTCTTCTACTTGTCCACAATCT

GACTGGGAATATTCTAGGCTATATGTGGTTCAAAGGGAATGGAGCACGTCCACATAAA

CAAATTAAGTTTTATGATGTAGACACAAAAGCATTTTCCACAGGGCCTCTAGCCACAG

GTCGAGAGACAATGTACCCCAATGGATCCCTGCTGTTCCAGAATGTCACGACGGAGT

ACGCAGGAAACTACACACTACTTGTCCTAAAAAGATCCTTGATATATGAAGTAGGAACT

GGACAAGTCCATGTATACAATCCAGGGTCAAATACCTCCATTGGAATAACTGTAATAC
```

-continued

```
ATAAAGACCCCAGTTACAGAGCCGAGCCCATTCCCGACAACCACCAAAAAGTGTGCG

ACATGAGCAAGTGTCCCAAATGCCCAGCTCCTGAGCTCCTGGGAGGGCCTTCGGTCT

TCATCTTCCCCCCGAATCCCAAGGACACCCTCATGATCACCCGAACACCCGAGGTCA

CCTGCGTGGTGGTGGATGTGAGCCAGGAGAACCCTGATGTCAAGTTCAACTGGTACA

TGGACGGGGTGGAGGTGCGCACAGCCACGACGAGGCCGAAGGAGGAGCAGTTCAA

CAGCACTTACCGCGTGGTCAGCGTCCTCCGCATCCAGCACCAGGACTGGCTGTCAG

GAAAGGAGTTCAAGTGTAAGGTCAACAACCAAGCCCTCCCACAACCCATCGAGAGGA

CCATCACCAAGACCAAAGGGCGGTCCCAGGAGCCGCAAGTGTACGTCCTGGCCCCA

CACCCAGACGAGCTGTCCAAGAGCAAGGTCAGCGTGACCTGCCTGGTCAAGGACTTC

TACCCACCTGAAATCAACATCGAGTGGCAGAGTAATGGGCAGCCAGAGCTGGAGACC

AAGTACAGCACCACCCAAGCCCAGCAGGACAGCGACGGGTCCTACTTCCTGTACAGC

AAGCTCTCCGTGGACAGGAACAGGTGGCAGCAGGGAACGACATTCACGTGTGGGGT

GATGCACGAGGCTCTCCACAATCACTACACACAGAAGAACGTCTCCAAGAACCCGGG

TAAATGA
```

SEQUENCE ID NO: 6 provides the open reading frame for the equine Fc tag forming part of SEQUENCE ID NO: 5

Equine Fc ORF

SEQUENCE ID NO: 6

```
ATGCAATCACCCTCAGGCCCTGCTCACAGAGGATGTGTCCCTTGGCAGGCGCTCCTC

TTGGCAGTCTCAATCTTAGCCTTCTGGAACCTGCCCGCCACTGTCCAGTTCACTATTG

AGTCGGTGCCGAACAATGTTACTGAAGGAAAGGATGTTCTTCTACTTGTCCACAATCT

GACTGGGAATATTCTAGGCTATATGTGGTTCAAAGGGAATGGAGCACGTCCACATAAA

CAAATTAAGTTTTATGATGTAGACACAAAAGCATTTTCCACAGGGCCTCTAGCCACAG

GTCGAGAGACAATGTACCCCAATGGATCCCTGCTGTTCCAGAATGTCACGACGGAGT

ACGCAGGAAACTACACACTACTTGTCCTAAAAAGATCCTTGATATATGAAGTAGGAACT

GGACAAGTCCATGTATACAATCCAGGGTCAAATACCTCCATTGGAATAACTGTAATAC

ATAAAGACCCCAGTTACAGAGCCGAGCCCATTCCCGACAACCACCAAAAAGTGTGCG

ACATGAGCAAGTGTCCCAAATGCCCAGCTCCTGAGCTCCTGGGAGGGCCTTCGGTCT

TCATCTTCCCCCCGAATCCCAAGGACACCCTCATGATCACCCGAACACCCGAGGTCA

CCTGCGTGGTGGTGGATGTGAGCCAGGAGAACCCTGATGTCAAGTTCAACTGGTACA

TGGACGGGGTGGAGGTGCGCACAGCCACGACGAGGCCGAAGGAGGAGCAGTTCAA

CAGCACTTACCGCGTGGTCAGCGTCCTCCGCATCCAGCACCAGGACTGGCTGTCAG

GAAAGGAGTTCAAGTGTAAGGTCAACAACCAAGCCCTCCCACAACCCATCGAGAGGA

CCATCACCAAGACCAAAGGGCGGTCCCAGGAGCCGCAAGTGTACGTCCTGGCCCCA

CACCCAGACGAGCTGTCCAAGAGCAAGGTCAGCGTGACCTGCCTGGTCAAGGACTTC

TACCCACCTGAAATCAACATCGAGTGGCAGAGTAATGGGCAGCCAGAGCTGGAGACC

AAGTACAGCACCACCCAAGCCCAGCAGGACAGCGACGGGTCCTACTTCCTGTACAGC

AAGCTCTCCGTGGACAGGAACAGGTGGCAGCAGGGAACGACATTCACGTGTGGGGT

GATGCACGAGGCTCTCCACAATCACTACACACAGAAGAACGTCTCCAAGAACCCGGG

TAAATGA
```

The terms "PSG1" and "CC49" also includes variants which are proteins having amino acid sequences which are substantially identical to wild-type PSG1 or CC49 protein, typically human wild-type PSG1 and equine wild-type CC49 protein. Thus, for example, the term should be taken to include proteins or polypeptides that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Typically, proteins which have been altered by substitution or deletion of catalytically-important residues will be excluded from the term "variant". Details of such catalytically-important residues will be well known to those skilled in the field of protein modelling. Generally, the variant will have at least 70% amino acid sequence homology, preferably at least 80% sequence homology, more preferably at least 90% sequence homology, and ideally at least 95%, 96%, 97%, 98% or 99% sequence homology with wild-type protein (excluding the signal peptide as recited above). In this context, sequence homology comprises both sequence identity and similarity, i.e. a polypeptide sequence that shares 70% amino acid homology with wild-type protein is one in which any 70% of aligned residues are either identical to, or conservative substitutions of, the corresponding residues in wild-type protein. As regards PSG1, specific variants included within the scope of the invention are the mutant PSG1 proteins identified in International Patent Application Publication Number WO2017049082, in paragraphs 25 to 38. The terms also include PSG1 or CC49 proteins modified with a tag such as an Fc tag, including human or equine Fc tags. The Fc tags may be modified to exhibit increased plasma half-life and/or stability; such Fc tags are known from the literature and are described herein. Examples of modifications to human Fc tags that include the triple substitution YTE (M252Y/S254T/T256E) in the CH2 domain and (H433K/N434F) in the CH3 domain to increase stability and half-life. In one embodiment, the invention provides CC49 protein modified with an Fc tag, typically an Fc tag derived from an equine antibody, typically an equine IgG antibody.

PSG1 or CC49 for use in the invention may be generated wholly or partly by chemical synthesis or by expression from nucleic acid (i.e. recombinant). For example, the protein of and for use in the present invention can be readily prepared according to well-established, standard liquid or, preferably, solid-phase protein synthesis methods known in the art (see, for example, J. M. Stewart and J. D. Young, Solid Phase Peptide Synthesis, 2nd edition, Pierce Chemical Company, Rockford, Illinois (1984), in M. Bodansky and A. Bodansky, The Practice of Peptide Synthesis, Springer Verlag, New York (1984). When necessary, any of the proteins employed in the invention can be chemically modified to increase their stability. A chemically modified protein or a protein analog includes any functional chemical equivalent of the protein characterized by its increased stability and/or efficacy and/or half-life in vivo or in vitro in respect of the practice of the invention. The term protein analog also refers to any amino acid derivative of a protein as described herein. A protein analog can be produced by procedures that include, but are not limited to, modifications to side chains, incorporation of unnatural amino acids and/or their derivatives during protein synthesis and the use of cross-linkers and other methods that impose conformational constraint on the proteins or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NaBH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tyrosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Protein structure modification includes the generation of retro-inverso proteins comprising the reversed sequence encoded by D-amino acids. Changes may be those that reduce susceptibility to proteolysis, reduce susceptibility to oxidation, alter binding affinity of the variant sequence (typically desirably increasing affinity), and/or confer or modify other physicochemical or functional properties on the associated variant/analog protein.

In this specification, the term "sequence identity" should be understand to comprise both sequence identity and similarity, i.e. a variant (or homolog) that shares 70% sequence identity with a reference sequence is one in which any 70% of aligned residues of the variant (or homolog) are identical to, or conservative substitutions of, the corresponding residues in the reference sequence across the entire length of the sequence. Sequence identity is the amount of characters which match exactly between two different sequences. Hereby, gaps are not counted and the measurement is relational to the shorter of the two sequences. In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence. This alignment and the percent homology or sequence identity can be determined using software programs known in the art, for example, one alignment program is BLAST, using default parameters. Details of these programs can be found at the following Internet address: http://www.ncbi.nlm.nih.gov/blast/Blast.cgi.

The term "PSG1" also includes PSG1 protein that is modified other than by insertion, deletion or substitution of an amino acid residue by modification with a functional group (modified proteins). Likewise, the term "CC49" also includes CC49 protein that is modified other than by insertion, deletion or substitution of an amino acid residue by modification with a functional group (modified proteins).

As used herein, the term "wound" should be understood to mean a wound or a scar formed as a result of a wound. The scar may be a hypertrophic scar or a keloid scar.

As used herein, the term "cutaneous wound" refers to wound in the skin and optionally underlying tissue of a mammal.

As used herein, the terms "epithelialisation" and "re-epithelialisation" as applied to a wound refers to a process in which an open wound or scar such as a keloid scar of the skin is covered by epithelial (keratinocytes) cells, which optionally migrate from the wound periphery. The methods of the invention relate to treatment of wounds, scars left by wounds, keloid scars, and wounds caused by excision of scars especially hypertrophic scars or scarring. The methods of the invention also include treatment of burns or scarring caused by burns.

As used herein, the term "PSG1 topical formulation" refers to a formulation of PSG1 suitable for topical administration to the skin of a mammal. The topical composition may be presented in a formulation selected from the group comprising creams, multiple emulsions, anhydrous compositions, aqueous dispersions, oils, milks, balsams, foams, lotions, gels, cream gels, hydro-alcoholic solutions, hydro-glycolic solutions, cosmetic, personal care product, hydro-gels, liniments, sera, soaps, dusting powder, paste, semi-solid formulations, liniments, serums, shampoo, conditioner, ointments, any rinse off formulation, talc, mousses, powders, sprays, aerosols, solutions, suspensions, emulsions, syrups, elixirs, polysaccharide films, patches, gel patches, bandages, an adhesive system, water-in-oil emulsions, oil-in-water emulsions, and silicone emulsions. The topical composition of the invention is administered in a cosmetically or pharmaceutically effective amount. In other words, in an amount that is non-toxic but sufficient amount to provide the desired effect. It will be appreciated that a person skilled in the art would be capable of determining an appropriate dose of the topical compositions of the invention to administer without undue experimentation. Alternatively, a physician will determine the actual dose that is most suitable for a patient depending on the particular condition, disease or disorder to be treated or cared for and the age, body weight and/or health of the person. It will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can, of course, be individual instances where higher or lower dosage ranges are merited, and such are within the scope of this invention. For example, the composition may be administered at a dose of from 0.01 to 50 mg/kg body weight, such as from 0.1 to 30 mg/kg, more preferably from 0.1 to 20 mg/kg body weight, more preferably from 0.1 to 10 mg/kg body weight, preferably 0.1 to 5 mg/kg body weight. In an exemplary embodiment, one or more doses of 10 to 300 mg/day or more preferably, 10 to 150 mg/day, will be administered to the patient. For injections into the tissue (intra-articular, etc) a dosage of 0.01-1.0 mg, preferably 0.05-0.5 mg, and ideally about 0.1 mg, is envisaged. The amount and the frequency is as best suited to the purpose. The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day. In an embodiment of the current invention, the emulsion contains a lipid or oil. The emulsion may be, but is not limited to, oil-in-water, water-in-oil, water-in-oil-in-water and oil-in-water-in-silicone emulsions. The emulsion may contain a humectant. The emulsion may contain an anti-foaming agent, such as silicone. The emulsion may have any suitable viscosity. Emulsions may further contain an emulsifier and/or an anti-foaming agent. Methods of preparing an emulsion are known to a person skilled in the art.

The active agent (PSG1 or CC49) is used in the topical or pharmaceutical composition of this invention at a pharmaceutically or therapeutically effective concentrations to achieve the desired effect; in a preferred form with regards to the total weight of the composition, between 0.00000001% (in weight) and 100% (in weight); typically between 0.00000001% (in weight) and 40% (in weight); preferably between 0.000001% (in weight) and 15% (in weight), more preferably between 0.0001% (in weight) and 10% (in weight) and even more preferably between 0.0001% (in weight) and 5% (in weight). Ideally, the PSG1 is preferably used from about 0.00001% w/w to about 0.5% w/w, and more preferably from 0.00005 w/w to about 0.05 w/w, and most preferably from about 0.0001 w/w to about 0.01 w/w of the composition. Ideally, the PSG1 or CC49 is preferably used from about 0.0001% w/w to about 0.004% w/w of the composition.

The composition of the invention may be administered individually or in combination with other pharmacologically active agents. It will be understood that such combination therapy encompasses different therapeutic regimens, including, without limitation, administration of multiple agents together in a single dosage form or in distinct, individual dosage forms. If the agents are present in different dosage forms, administration may be simultaneous or near-simultaneous or may follow any predetermined regimen that encompasses administration of the different agents. The suitable active agents may be as described herein.

In some embodiments of the current invention, the composition may be delivered via any one of liposomes, mixed liposomes, oleosomes, niosomes, ethosomes, millicapsules, capsules, macrocapsules, nanocapsules, nanostructured lipid carriers, sponges, cyclodextrins, vesicles, micelles, mixed micelles of surfactants, surfactant-phospholipid mixed micelles, millispheres, spheres, lipospheres, particles, nano-spheres, nanoparticles, milliparticles, solid nanopartciles as well as microemulsions including water-in-oil microemulsions with an internal structure of reverse micelle and nanoemulsions microspheres, microparticles.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235, 871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

These delivery systems may be adapted to achieve a greater penetration of the compound and/or peptides of the invention. This may improve pharmacokinetic and pharmacodynamics properties. The delivery system may be a sustained release system wherein the compound or peptide of the invention is gradually released during a period of time and preferably with a constant release rate over a period of time. The delivery systems are prepared by methods known in the art. The amount of peptide contained in the sustained release system will depend on where the composition is to be delivered and the duration of the release as well as the type of the condition, disease and/or disorder to be treated or cared for.

The compound of the invention may be administered by oral administration. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The compound may be coated, or co-administered with, a material to prevent its inactivation. The coating may be configured to protect the active agent during transit through the stomach and release the active agent in the ileum.

As used herein, the term "condition characterised by loss of, or damage to, cartilage" refers to osteoarthritis or cartilage damaged by trauma, for example a fall or sports injury, wear and tear, or other disease processes. The methods of the invention are directed to treating the condition by slowing or inhibiting the loss of cartilage, and/or by causing growth and/or repair of cartilage. Treatment of conditions characterised by damage to or degeneration of articular cartilage are envisaged.

The methods of the invention may involve administering a nucleic acid construct configured to express in-vivo the active agent (PSG1 or CC49). As used herein, the term "PSG1 expression vector" or "CC49 expression vector" may be any suitable vector, including chromosomal, non-chromosomal, and synthetic nucleic acid vectors (a nucleic acid sequence comprising a suitable set of expression control elements) suitable for expression of PSG1 or CC49 (or a modified version thereof such as Fc-tagged protein) in a cell. Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, the PSG1 or CC49 amino acid sequence-encoding nucleic acid molecule is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. Nos. 5,589,466 and 5,973,972). In one embodiment, the DNA comprises an expression control sequence.

In any embodiment, the vector is suitable for expression of the protein in a bacterial cell. Examples of such vectors include expression vectors such as BlueScript (Stratagene), pIN vectors (Van Heeke & Schuster, 1989, J Biol Chem 264, 5503-5509), pET vectors (Novagen, Madison, Wis.) and the like. In any embodiment, the expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed., 1987, Current Protocols in Molecular Biology, Greene Publishing and Wiley InterScience New York; and Grant et al., 1987, Methods in Enzymol 153, 516-544). In other embodiments, the expression vector is suitable for expression in baculovirus-infected insect cells. (Kost, T; and Condreay, J P, 1999, Current Opinion in Biotechnology 10 (5): 428-33.)

Expression control sequences are engineered to control and drive the transcription of genes of interest, and subsequent expression of proteins in various cell systems. Plasmids combine an expressible gene of interest with expression control sequences (i.e. expression cassettes) that comprise desirable elements such as, for example, promoters, enhancers, selectable markers, operators, etc. In an expression vector of the invention, PSG1 or CC49 amino acid sequence-encoding nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to permit transcription of the protein-encoding nucleotide sequence when the appropriate signals are present. The expression of the protein-encoding nucleotide sequence may be placed under control of any promoter or enhancer element known in the art. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters). In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operably linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable. Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin@ resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

In certain embodiments, the vector comprises one or more selectable marker genes selected from the group consisting of bla, bls, bsd, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), or yellow fluorescent protein (YFP).

For the purposes of this invention, gene expression in eukaryotic cells may be tightly regulated using a strong promoter that is controlled by an operator that is in turn regulated by a regulatory protein, which may be a recombinant "regulatory fusion protein" (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene in such a way that the gene may be regulated by the binding of the RFP to the operator and, as a result, prevents or allows transcription of the gene of interest, i.e. a nucleotide encoding a polypeptide of the invention. A number of operators in prokaryotic cells and bacteriophage have been well characterized (Neidhardt, ed., *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide, and the lactose and tryptophan operators, which bind the repressor proteins encoded by the Lad and trpR genes of *E. coli*. These also include the bacteriophage operators from the lambda PR and the phage P22 ant/mnt genes, which bind the repressor proteins encoded by lambda cl and P22 arc. In some embodiments, when the transcription blocking domain of the RFP is a restriction enzyme, such as Notl, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.)

The vectors of the invention may also employ Cre-lox recombination tools to facilitate the integration of a gene of interest into a host genome. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (See, e.g. Araki et al., 1995, PNAS 92:160-4; Nagy, A. et al., 2000, Genesis 26:99-109; Araki et al., 2002, Nuc Acids Res 30(19):e103; and US20100291626A1, all of which are herein incorporated by reference). In another recombination strategy, yeast-derived FLP recombinase may be utilized with the consensus sequence FRT (see also, e.g. Dymecki, S. M., 1996, PNAS 93(12): 6191-6196).

As used herein, the term "host cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g. *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, mammalian cells, human cells, or cell fusions such as, for example, hybridomas or quadromas. In certain embodiments, the cell is a human, equine, canine, feline, supine, monkey, ape, hamster, rat or mouse cell. In other embodiments, the cell is eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, W138, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell. In one embodiment, the host cell is a bacterium.

As used herein, the term "transformed cell" refers to a host cell comprising a nucleic acid stably integrated into the cellular genome that comprises a nucleotide sequence coding for expression of a PSG1 or CC49 protein. In another embodiment, the present invention provides a cell comprising a non-integrated (i.e., episomal) nucleic acid, such as a plasmid, cosmid, phagemid, or linear expression element, which comprises a sequence coding for expression of a PSG1 or CC49 protein. In other embodiments, the present invention provides a cell line produced by stably transfecting a host cell with a plasmid comprising an expression vector of the invention.

As used herein, the term "engineered" as applied to a cell means genetically engineered using recombinant DNA technology, and generally involves the step of synthesis of a suitable expression vector (see above) and then transfecting the expression vector into a host cell (generally stable transfection).

As used herein, the term "heterologous expression" refers to expression of a nucleic acid in a host cell that does not naturally have the nucleic acid. Insertion of the nucleic acid into the heterologous host is performed by recombinant DNA technology.

As used herein, the term "administering" in the context of treating should be taken to include any form of delivery that is capable of delivering the active agent to the subject, including intravenous delivery, oral delivery, intramuscular delivery, and inhaled delivery. Methods for achieving these means of delivery will be well known to those skilled in the art of drug delivery, and include:

Delivered intrathecially by mini-osmotic pump. (ref: Ignacio et al., Ann. N.Y. Acad. Sci. 2005, 1053: 121-136).

Intramuscular delivery directly into muscle(s) by syringe or mini osmotic pump (Azzouz et al., Nat Med. 2005; 11(4):429-33).

Intraperitoneal—for systemic administration—directly administered to peritoneum by syringe or mini osmotic pump (Kieran et al., Nat Med 2004; 10(4):402).

Subcutaneous—for systemic administration—directly administered below the skin by syringe (Reinholz et al., Exp Neurol. 1999; 159(1):204-16).

Implant—can be prepared in an implant (eg small silicon implant) that will release Active. Implant can be placed at muscles (Kieran and Greensmith, 2004 Neurosci 125(2):427-39).

Modified Proteins

In any embodiment, the PSG1 or CC49 protein (including protein fragments and variants) may be a modified protein. The term "modified protein" is used interchangeably with the term "derivative of the protein". In any embodiment, the term "modified protein" means a protein that is modified to exhibit one or more of the following properties compared with the unmodified protein: increase plasma half-life; increase the lipophilicity of the protein; decrease the renal clearance of the modified protein; increase the activity of the modified protein, and increase the resistance of the modified protein to proteolytic degradation (i.e. by mammalian and especially human gastrointestinal proteases). Various methods of modifying a protein of the invention to exhibit these properties are disclosed herein, including conjugating the protein with a binding partner (for example an albumin binding small molecule, large polymer, long life plasma protein, or antibody or antibody-fragment), cyclisation, addition of N- or C-terminal, or side chain, protecting groups, replacing one or more L-amino acids with D-isomers, amino acid modification, increased plasma protein binding, increased albumin binding. The modified protein includes but is not limited to a protein which has been substituted with one or more groups as defined herein, or conjugated with a binding partner, or cyclized. Generally, the protein is modified to increase it half-life in-vivo in an animal. Various methods of modification are provided below.

In any embodiment, the modification may be any modification that provides the proteins and or the composition of the invention with an increased ability to penetrate a cell. In any embodiment, the modification may be any modification that increases the half-life of the composition or proteins of the invention. In one embodiment, the modification may be any modification that increases activity of the composition or proteins. In any embodiment, the modification may be any modification that increases selectivity of the composition or proteins.

In any embodiment, the group is a protecting group. The protecting group may be an N-terminal protecting group, a C-terminal protecting group or a side-chain protecting group. The protein may have one or more of these protecting groups.

The person skilled in the art is aware of suitable techniques to react amino acids with these protecting groups. These groups can be added by preparation methods known in the art, for example the methods as outlined in paragraphs [0104] to [0107] of US2014120141. The groups may remain on the protein or may be removed. The protecting group may be added during synthesis.

In any embodiment of the invention the proteins may be substituted with a group selected from one or more straight chain or branched chain, long or short chain, saturated, or unsaturated, substituted with a hydroxyl, amino, amino acyl, sulfate or sulphide group or unsubstituted having from 1 to 29 carbon atoms. N-acyl derivatives include acyl groups derived from acetic acid, capric acid, lauric acid, myristic acid, octanoic acid, palmitic acid, stearic acid, behenic acid, linoleic acid, linolenic acid, lipoic acid, oleic acid, isosteric acid, elaidoic acid, 2-ethylhexaneic acid, coconut oil fatty acid, tallow fatty acid, hardened tallow fatty acid, palm kernel fatty acid, lanolin fatty acid or similar acids. These may be substituted or unsubstituted. When substituted they are preferably substituted with hydroxyl, or sulphur containing groups such as but not limited to $SO_3H$, SH, or S—S.

In any embodiment of the current invention, the protein is R1-X— R2.

R1 and/or R2 groups respectively bound to the amino-terminal (N-terminal) and carboxyl-terminal (C-terminal) of the protein sequence.

In one embodiment, the protein is R1-X. Alternatively, the protein is X— R2.

Preferably, R1 is H, C1-4 alkyl, acetyl, benzoyl or trifluoroacetyl;

X is the protein active of the invention (e.g. PSG1 or Fc-tagged PSG1, CC49 or Fc-tagged CC49);

R2 is OH or $NH_2$.

In any embodiment, R1 is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, Tert-butyloxycarbonyl, 9-fluorenylmethyloxycarbonyl (Fmoc) and R5-CO—, wherein R5 is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R2 is selected from the group formed by —NR3R4, —OR3 and —SR3, wherein R3 and R4 are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that R1 and R2 are not α-amino acids.

In accordance with another preferred embodiment, R2 is —NR3R4, —OR3 or —SR3 wherein R3 and R4 are independently selected from the group formed by H, substituted or unsubstituted C1-C24 alkyl, substituted or unsubstituted C2-C24 alkenyl, Tert-butyloxycarbonyl, 9-fluorenylmethyloxycarbonyl (Fmoc), substituted or unsubstituted C2-C 24 alkynyl, substituted or unsubstituted C3-C 24 cycloalkyl, substituted or unsubstituted C 5-C24 cycloalkenyl, substituted or unsubstituted C8-C24 cycloalkynyl, substituted or unsubstituted C 6-C 30 aryl, substituted or unsubstituted C7-C24 aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, R3 and R4 can be bound by a saturated or unsaturated carbon-carbon bond, forming a cycle with the nitrogen atom. More preferably R 2 is —NR3R4 or —OR 3, wherein R3 and R4 are independently selected from the group formed by H, substituted or unsubstituted C1-C 24 alkyl, substituted or unsubstituted C2-C24 alkenyl, substituted or unsubstituted C2-C24 alkynyl, substituted or unsubstituted C3-C10 cycloalkyl, substituted or unsubstituted C6-C15 aryl and substituted or unsubstituted heterocyclyl of 3-10 members, substituted or unsubstituted heteroarylalkyl with a ring of 3 to 10 members and an alkyl chain of 1 to 6 carbon atoms. More preferably R3 and R4 are selected from the group formed by H, methyl, ethyl, hexyl, dodecyl, or hexadecyl. Even more preferably R3 is H and R4 is selected from the group formed by H, methyl, ethyl, hexyl, dodecyl, or hexadecyl. In accordance with an even more preferred embodiment, R2 is selected from —OH and —NH$_2$.

In accordance with another embodiment of this invention R1 is selected from the group formed by H, acetyl, lauroyl, myristoyl or palmitoyl, and R2 is —NR3R 4 or —OR3 wherein R3 and R4 are independently selected from H, methyl, ethyl, hexyl, dodecyl and hexadecyl, preferably R2 is —OH or —NH$_2$. More preferably, R1 is acetyl or palmitoyl and R2 is —NH$_2$.

In a preferred embodiment, the acyl (or acetyl) group is bound to the N-terminal end of at least one amino acid of the protein.

In any embodiment of the invention, the protein is modified to comprise a side chain protecting group. The side chain protecting group may be one or more of the group comprising benzyl or benzyl based groups, t-butyl-based groups, benzyloxy-carbonyl (Z) group, and allyloxycarbonyl (alloc) protecting group. The side chain protecting group may be derived from an achiral amino acid such as achiral glycine. The use of an achiral amino acid helps to stabilise the resultant protein and also facilitate the synthesis route of the present invention. Preferably, the protein further comprises a modified C-terminus, preferably an amidated C-terminus. The achiral residue may be alpha-aminoisobutyric acid (methylalaine). It will be appreciated that the specific side chain protecting groups used will depend on the sequence of the protein and the type of N-terminal protecting group used. In one embodiment of the invention the protein is conjugated, linked or fused to one or more polyethylene glycol polymers or other compounds, such as molecular weight increasing compounds. The molecular weight increasing compound is any compound that will increase the molecular weight, typically by 10% to 90%, or 20% to 50% of the resulting conjugate and may have a molecular weight of between 200 and 20, 000, preferably between 500 and 10, 000. The molecular weight increasing compound may be PEG, any water-soluble (amphiphilic or hydrophilic) polymer moiety, homo or co-polymers of PEG, a monomethyl-substituted polymer of PEG (mPEG) and polyoxyethylene glycerol (POG), polyamino acids such as poly-lysine, poly-glutamic acid, poly-aspartic acid, particular those of L conformation, pharmacologically inactive proteins such as albumin, gelatin, a fatty acid, olysaccharide, a lipid amino acid and dextran. The polymer moiety may be straight chained or branched and it may have a molecular weight of 500 to 40000 Dalton (DA), 5000 to 10000 Da, 10000 to 5000, Da. The compound may be any suitable cell penetrating compound, such as tat protein, penetratin, pep-1. The compound may be an antibody molecule. The compound may be a lipophilic moiety or a polymeric moiety.

The lipophilic substituent and polymeric substituents are known in the art. The lipophilic substituent includes an acyl group, a sulphonyl group, an N atom, an O atom or an S atom which forms part of the ester, sulphonyl ester, thioester, amide or sulphonamide. The lipophilic moiety may include a hydrocarbon chain having 4 to 30 C atoms, preferably between 8 and 12 C atoms. It may be linear or branched, saturated or unsaturated. The hydrocarbon chain may be further substituted. It may be cycloalkane or heterocycloalkane. The protein may be modified at the N-terminal, C-terminal or both. The polymer or compound is preferably linked to an amino, carboxyl or thiol group and may be linked by N-termini or C-termini of side chains of any amino acid residue. The polymer or compound may be conjugated to the side chain of any suitable residue.

The polymer or compound may be conjugated via a spacer. The spacer may be a natural or unnatural amino acid, succinic acid, lysyl, glutamyl, asparagyl, glycyl, beta-alanyl, gamma-amino butanoyl.

The polymer or compound may be conjugated via an ester, a sulphonyl ester, a thioester, an amide, a carbamate, a urea, a sulphonamide.

A person skilled in the art is aware of suitable means to prepare the described conjugate.

Proteins can be chemically modified by covalent conjugation to a polymer to increase their circulating half-life, for example. Exemplary polymers and methods to attach such polymers to proteins are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties.

The proteins of the invention may be subjected to one or more modifications for manipulating storage stability, pharmacokinetics, and/or any aspect of the bioactivity of the protein, such as, e.g., potency, selectivity, and drug interaction. Chemical modification to which the proteins may be subjected includes, without limitation, the conjugation to a protein of one or more of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives. PEG conjugation of proteins at Cys residues is disclosed, e.g., in Goodson, R. J. & Katre, N. V. (1990) Bio/Technology 8, 343 and Kogan, T. P. (1992) Synthetic Comm. 22, 2417.

Modified proteins also can include sequences in which one or more residues are modified (i.e., by phosphorylation, sulfation, acylation, amindation, PEGylation, etc.), and mutants comprising one or more modified residues with respect to a parent sequence. Amino acid sequences may also be modified with a label capable of providing a detectable signal, either directly or indirectly, including, but not limited to, radioisotope, fluorescent, and enzyme labels. Fluorescent labels include, for example, Cy3, Cy5, Alexa, BODIPY, fluorescein (e.g., FluorX, DTAF, and FITC), rhodamine (e.g., TRITC), auramine, Texas Red, AMCA blue, and Lucifer Yellow. Preferred isotope labels include 3H, 14C, 32 P, 35S, 36Cl, 51Cr, 57Co, 58Co, 59Fe, 90Y, 125I, 131I, and 286Re. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

In an embodiment, the protein, variant and/or composition is modified to increase drug performance ability. In an embodiment, the protein, variant and/or composition is modified to increase stability, permeability, maintain potency, avoid toxicity and/or to increase half-life. The modification may be as described above. For example, the modification may be to protect the N and C-terminus, it may be a modified amino acid, cyclisation, replacement of an amino acid, and/or conjugation to macromolecules or large polymers or long life plasma proteins. Strategies to extend a half-life may be as described by Strohl, et al (BioDrugs, 2015), Schlapschy, et al (Protein Eng Des Sel. 2013), Podust, V N, et al (Protein Eng Des Sel. 2013), Zhang, L et al (Curr Med Chem. 2012), Gaberc-Porekar, V, et al (Curr Opin Drug Discov Devel. 2008). Examples include using PEGylation, lipidation (covalent binding of fatty acids to protein side chains), fusion to Fc domains and human serum albumin, fusion with a hydrophilic amino acid polymer, e.g. XTEN or PAS, and/or fusion with half-life extension proteins.

Proteins or proteins can comprise weak sites in their sequence which are prone to undergoing proteolytic breakage when in a proteolytic enriched environment, e.g. in the blood or gastrointestinal tract. In an embodiment, the protein, variant and/or composition comprises a modification of one or more weak sites such that the protein, variant and/or composition does not undergo proteolytic breakdown/cleavage or undergoes a decreased amount of proteolytic breakdown/cleavage compared to an unmodified protein or protein. Thus, the protein may be modified to increase the resistance of the modified protein to proteolytic degradation to mammalian gastrointestinal proteases. Suitable modifications are described in Diao et al (Clinical pharmacokinetics 52.10 (2013): 855-868).

Modification of proteins to extend the in-vivo half-life of the protein is described in the literature, for example:

Strategies to improve plasma half life time of protein and protein drugs. Werle M, Bernkop-Schnürch A. Amino Acids. 2006 June; 30(4):351-67.

Due to the obvious advantages of long-acting protein and protein drugs, strategies to prolong plasma half life time of such compounds are highly on demand. Short plasma half-life times are commonly due to fast renal clearance as well as to enzymatic degradation occurring during systemic circulation. Modifications of the protein/protein can lead to prolonged plasma half-life times. By shortening the overall amino acid amount of somatostatin and replacing L: -analogue amino acids with D: -amino acids, plasma half life time of the derivate octreotide was 1.5 hours in comparison to only few minutes of somatostatin. A PEG(2.40 K) conjugate of INF-alpha-2b exhibited a 330-fold prolonged plasma half-life time compared to the native protein. It was the aim of this review to provide an overview of possible strategies to prolong plasma half life time such as modification of N- and C-terminus or PEGylation as well as methods to evaluate the effectiveness of drug modifications.

Furthermore, fundamental data about most important proteolytic enzymes of human blood, liver and kidney as well as their cleavage specificity and inhibitors for them are provided in order to predict enzymatic cleavage of protein and protein drugs during systemic circulation.

Strategic Approaches to Optimizing Protein ADME Properties. Li Di AAPS J. 2015 January; 17(1): 134-143.

Strategies to Stabilize Proteins from Proteolysis

Many approaches are available to enhance stability of proteins through structure modification. Some approaches not only improve stability, but also enhance other ADME properties, e.g., cyclization can increase stability and permeability; conjugation to macromolecules can improve stability and reduce renal clearance. It is important to maintain potency and avoid toxicity while improving stability and ADME properties of proteins.

Protecting N- and C-Terminus

A number of proteolytic enzymes in blood/plasma, liver or kidney are exopeptidases, aminopeptidases and carboxypeptidases and they break down protein sequences from the N- and C-termini. Modification of the N- or/and C-termini can often improve protein stability. Many examples have reported that N-acetylation, and C-amidation increase resistance to proteolysis.

Replacing L-Amino Acids with D-Amino Acids

Substituting natural L-amino acids with non-natural D-amino acids decreases the substrate recognition and binding affinity of proteolytic enzymes and increases stability. One example is vasopressin, which contains an L-Arg and has a half-life of 10-35 min in humans. The D-Arg analog, desmopressin, has a half-life of 3.7 h in healthy human volunteers. In the study of a bicyclic protein inhibitor of the cancer-related protease urokinase-type plasminogen activator (uPA), replacement of a specific glycine with a D-serine not only improves potency by 1.8-fold but also increases stability by 4-fold in mouse plasma.

Modification of Amino Acids

Modification of natural amino acids can improve the stability of proteins by introducing steric hindrance or disrupting enzyme recognition. For example, gonadotropin-releasing hormone has a very short half-life (minutes), while buserelin, in which one Gly is replaced with a t-butyl-D-Ser and another Gly is substituted by ethylamide, has a much longer half-life in humans.

Cyclization

Cyclization introduces conformation constraint, reduces the flexibility of proteins, and increases stability and permeability. Depending on the functional groups, proteins can be cyclized head-to-tail, head/tail-to-side-chain, or side-chain-to-side-chain. Cyclization is commonly accomplished through lactamization, lactonization, and sulfide-based bridges. Disulfide bridges create folding and conformational constraints that can improve potency, selectivity, and stability. A number of disulfide bond-rich proteins are on the market or in preclinical or clinical development, e.g., linaclotide, lepirudin, and ziconotide.

Conjugation to Macromolecules

Conjugation to macromolecules (e.g., polyethylene glycol (PEG), albumin) is an effective strategy to improve stability of proteins and reduce renal clearance.

Renal Clearance

Many proteins exhibit promising in vitro pharmacological activity but fail to demonstrate in vivo efficacy due to very short in vivo half-life (minutes). The rapid clearance and short half-life of proteins hamper their development into successful drugs. The main causes of rapid clearance of proteins from systemic circulation are enzymatic proteolysis or/and renal clearance. The glomeruli have a pore size of ~8 nm, and hydrophilic proteins with MW<2-25 kDa are susceptible to rapid filtration through the glomeruli of the kidney. Since proteins are not easily reabsorbed through the renal tubule, they frequently have high renal clearance and short half-life. Other minor routes of protein clearance are endocytosis and degradation by proteasome and the liver. Comparison between systemic and renal clearance in animal models provides useful information on whether renal clearance is likely to be a major elimination pathway.

For renal-impaired patients, dose adjustment may be needed for protein drugs to avoid accumulation and higher drug exposure, as inappropriate dosing in patients with renal dysfunction can cause toxicity or ineffective therapy. Several strategies have been developed to reduce protein renal clearance and prolong half-life. These will be reviewed next.

Increase Plasma Protein Binding

Renal clearance of proteins is reduced when they are bound to membrane proteins or serum proteins. An example is the cyclic protein drug octreotide, a treatment for endocrine tumors, which has about 100 min half-life in humans due to binding to lipoproteins (fraction unbound 0.65)

Covalent Linkage to Albumin-Binding Small Molecules

Covalently attaching albumin-binding small molecules to proteins can reduce glomerular filtration, improve proteolytic stability, and prolong half-life by indirectly interacting with albumin through the highly bound small molecules.

Conjugation to Large Polymers

Conjugation of proteins to large synthetic or natural polymers or carbohydrates can increase their molecular weight and hydrodynamic volume, thus reducing their renal clearance. The common polymers used for protein conjugation are PEG, polysialic acid (PSA), and hydroxyethyl starch (HES).

Fusion to Long-Live Plasma Proteins

Plasma proteins, such as albumin and immunoglobulin (IgG) fragments, have long half-lives of 19-21 days in humans. Because of the high MW (67-150 kDa), these proteins have low renal clearance, and their binding to neonatal Fc receptor (FcRn) reduces the elimination through pinocytosis by the vascular epithelium. Covalent linkage of proteins to albumin or IgG fragments can reduce renal clearance and prolong half-life.

Fusion Proteins for Half-Life Extension of Biologics as a Strategy to Make Biobetters William R. Strohl BioDrugs. 2015; 29(4): 215-239.

Schlapschy, M, Binder, U, Borger, C et al. PASYlation: a biological alternative to PEGylation for extending the plasma half-life of pharmaceutically active proteins. Protein Eng Des Sel. 2013; 26(8):489-501.

Podust, VN, Sim, BC, Kothari, D et al. Extension of in vivo half-life of biologically active proteins via chemical conjugation to XTEN protein polymer. Protein Eng Des Sel. 2013; 26(11):743-53.

Zhang, L, Bulaj, G. Converting Proteins into Drug Leads by Lipidation. Curr Med Chem. 2012; 19(11):1602-18.

Gaberc-Porekar, V, Zore, I, Podobnik, B et al. Obstacles and pitfalls in the PEGylation of therapeutic proteins. Curr Opin Drug Discov Devel. 2008; 11(2):242-50.

Dr Ronald V. Swanson—Long live proteins evolution of protein half-life extension technologies and emerging hybrid approaches. From Drug Discovery World on line. Spring 2014

PEGylation

The attachment of long chains of the hydrophilic polymer polyethylene glycol to molecules of interest, PEGylation was originally conceived as a modification to prevent the recognition of foreign proteins by the immune system and, thereby, enable their utility as therapeutics. Once formed, antibodies against unmodified drugs can rapidly neutralise and clear protein drugs. Unexpectedly, PEGylation improved the pharmacokinetics of the proteins even in the absence of anti-drug antibodies1. Simply by making drug molecules larger, PEGylation led to the drug being filtered more slowly by the kidneys. The empirical observation that increasing size or hydrodynamic radius led to reduced renal clearance and increased half-life then became the dominant rationale for the PEGylation of protein and protein drugs. PEGylation can have a variety of effects on the molecule including making proteins or proteins more water-soluble and protecting them from degradation by proteolytic enzymes. PEGylation can also impact the binding of therapeutic proteins to their cognate cellular receptors, usually reducing the affinity. Changes in the size, structure and attachment mode of PEG polymers can affect the biological activity of the attached drug.

The first-generation PEGylation methods were filled with challenges. However, the chemistry of PEGylation is quite simple. The process involves the covalent attachment of polyethylene glycol chains to reactive side chains of a protein or protein. For example, PEG is easily attached to the -amino groups of lysine on the surface of proteins or proteins2. The reaction is pH-dependent. At high pH (8.0 or higher), lysine side chain amino groups are covalently attached to PEG through N-hydroxy succinimides. This method typically results in a family of products containing different numbers of PEG chains attached at different sites on a protein rather than a single discrete product3. The first approved PEGylated pharmaceuticals were Pegademase bovine (PEGylated bovine adenosine deamidase) as enzyme replacement therapy for severe combined immunodeficiency and Pegaspargase (PEGylated asparaginase) for treatment of acute lymphoblastic leukaemia1. These drugs were complex mixtures of various PEGylated species, but with improved properties for therapy over native enzymes, including increased serum half-life and decreased immunogenicity of the proteins. Due to the inherent polydispersity of the PEG, quality and batch-to-batch reproducibility was difficult. Despite this limitation, two PEGylated interferons, (Peginterferon alfa-2b and Peginterferon alfa-2a) that are heterogeneous populations of numerous mono-PEGylated positional isomers, have been FDA-approved for the treatment of hepatitis C. These drugs were brought to market in 2001 and 2002, respectively.

A variety of enhancements and variations have been made to the fundamental PEGylation technology. Second-generation PEGylation processes introduced the use of branched structures as well as alternative chemistries for PEG attachment. In particular, PEGs with cysteine reactive groups such as maleimide or iodoacetamide allow the targeting of the PEGylation to a single residue within a protein or protein reducing the heterogeneity of the final product but not eliminating it due to the polydispersity of the PEG itself.

While the original rationale for PEGylation was to reduce immunogenicity; nevertheless, there have been a few examples of immunogenic PEGylated proteins. One example is PEGylated urate oxidase, an enzyme that lowers the plasma urate level in patients with gout. In clinical trials, a relatively high percentage of patients with gout did not respond to the therapy and developed antibodies that were specific for PEG, but not for the uricase protein2. PEGylated liposomes, also generally thought to be non-immunogenic, have been found to be immunogenic in some studies. PEGylated liposomes elicit a strong anti-PEG immunoglobulin M (IgM) response. In addition, multiple injections of PEG-glucuronidase were shown to elicit the generation of specific anti-PEG IgM antibodies, thus accelerating the clearance of PEG-modified proteins from the body.

A major potential drawback of using PEG as a modifier is that it is non-biodegradable. The US Food and Drug Administration (FDA) has approved PEG for use as a vehicle in pharmaceuticals, including injectable, topical, rectal and nasal formulations. PEG shows little toxicity and is eliminated from the body intact by either the kidneys (for PEGs<30 kDa) or in the feces (for PEGs>20 kDa)1. Repeated administration of some PEGylated proteins to animals has resulted in observations of renal tubular cellular vacuolation. Recently, vacuolation of choroid plexus epithelial cells has also been seen in toxicity studies with proteins conjugated with large (≥40 kDa) PEGs. The choroid plexus epithelial cells produce cerebrospinal fluid and form the blood CSF barrier. The long-term negative consequences of cellular vacuolation are unclear, but it does represent an undesirable consequence for some potential therapeutics. One possible alternative would be substitution of a biodegradable polymer in place of PEG. Polymers, such as hydroxyethyl starch (HES) are a possible alternative. HES is non-toxic and biodegradable and used as a blood expander. A process of HESylation would function similarly to PEGylation in reducing renal clearance through increasing a protein's hydrodynamic radius but may confer a lower propensity for accumulation due to biodegradability. However, HES and other proposed biodegradable polymer PEG alternatives are, like PEG, polydisperse making characterisation of the final product and metabolites difficult. One emerging solution which mitigates both concerns is to use defined polyproteins as the polymer component; this approach will be discussed later in the article.

Lipidation

A second major chemical modification method to increase protein half-life is lipidation which involves the covalent binding of fatty acids to protein side chains4. Originally conceived of and developed as a method for extending the half-life of insulin, lipidation shares the same basic mechanism of half-life extension as PEGylation, namely increasing the hydrodynamic radius to reduce renal filtration. However, the lipid moiety is itself relatively small and the effect is mediated indirectly through the non-covalent binding of the lipid moiety to circulating albumin. A large (67 KDa) and highly abundant protein in human serum (35-50 g/L), albumin naturally functions to transport molecules, including lipids, throughout the body. Binding to plasma proteins can also protect the protein from attacks by peptidases through steric hindrance, again akin to what is seen with PEGylation. One consequence of lipidation is that it reduces the water-solubility of the protein but engineering of the linker between the protein and the fatty acid can modulate this, for example by the use of glutamate or mini PEGs within the linker. Linker engineering and variation of the lipid moiety can affect self-aggregation which can contribute to increased half-life by slowing down biodistribution, independent of albumin5.

Following the pioneering work with insulin6, lipidation of a variety of proteins has been explored, particularly proteins within the diabetes space including human glucagon-like protein-1 (GLP-1) analogues, glucose-dependent insulinotropic polyprotein and GLP-1R/Glucagon receptor coagonists among others. Two lipidated protein drugs are currently FDA-approved for use in humans. These are both long-acting anti-diabetics, the GLP-1 analogue liraglutide and insulin detemir.

A potentially pharmacologically-relevant difference between PEGylation and lipidation is that the therapeutically active protein is covalently linked to the much larger PEG, whereas the smaller fatty acyl-protein conjugate is non-covalently associated with the larger albumin, bound and unbound forms existing in equilibrium. This can result in differences in biodistribution that may result in different pharmacology as access to receptors localised in different tissues may elicit differential effects. In some cases, more restricted biodistribution may be desirable, while in others, greater tissue penetration may be important. An interesting variation of the PEG approach which addresses this issue has been developed by Santi et al in which releasable PEG conjugates with predictable cleavage rates are utilised7.

PEGylation and lipidation both confer protection against proteases and peptidases by shielding through steric hindrance and extend circulating half-life through increased hydrodynamic radius, directly or indirectly. Both methods utilise chemical conjugation and are flexible in that they are agnostic to the means used to generate the protein they are modifying, whether biologically or synthetically produced. An advantage of using synthetic proteins is that they can incorporate non-natural amino acids designed to address a number of specific issues including instability due to known proteolytic cleavage liabilities. They can also be more flexible in terms of the choice of attachment site which is critical if activity or potency is highly dependent on the free termini or a modified residue such as a C terminal amide.

Classical Genetic Fusions: Fc and HSA

Classical genetic fusions to long-lived serum proteins offer an alternative method of half-life extension distinct from chemical conjugation to PEG or lipids. Two major proteins have traditionally been used as fusion partners: antibody Fc domains (in particular human and equine IgG1 Fc tags) and human serum albumin (HAS) Fc fusions involve the fusion of proteins, proteins or receptor exodomains to the Fc portion of an antibody. Both Fc and albumin fusions achieve extended half-lives not only by increasing the size of the protein drug, but both also take advantage of the body's natural recycling mechanism: the neonatal Fc receptor, FcRn. The pH-dependent binding of these proteins to FcRn prevents degradation of the fusion protein in the endosome. Fusions based on these proteins can have half-lives in the range of 3-16 days, much longer than typical PEGylated or lipidated proteins. Fusion to antibody Fc can improve the solubility and stability of the protein or protein drug. An example of a protein Fc fusion is dulaglutide, a GLP-1 receptor agonist currently in late-stage clinical trials. Human serum albumin, the same protein exploited by the fatty acylated proteins is the other popular fusion partner. Albiglutide is a GLP-1 receptor agonist based on this platform. A major difference between Fc and albumin is the dimeric nature of Fc versus the monomeric structure of HAS leading to presentation of a fused protein as a dimer or a monomer depending on the choice of fusion partner. The dimeric nature of a protein Fc fusion can produce an avidity effect if the target receptors are spaced closely enough together or are themselves dimers. This may be desirable or not depending on the target. In one embodiment, the Fc domain is engineered to include mutations. Methods of engineering mutations into Fc domains are described in Rath et al (2013; doi=10.3109/07388551.2013.834293).

Designed Polyprotein Fusions: XTEN and PAS

An intriguing variation of the recombinant fusion concept has been the development of designed low complexity sequences as fusion partners, basically unstructured, hydrophilic amino acid polymers that are functional analogs of PEG. The inherent biodegradability of the polyprotein platform makes it attractive as a potentially more benign alternative to PEG. Another advantage is the precise molecular structure of the recombinant molecule in contrast to the polydispersity of PEG. Unlike HSA and Fc protein fusions, in which the three-dimensional folding of the fusion partner needs to be maintained, the recombinant fusions to unstructured partners can, in many cases, be subjected to higher temperatures or harsh conditions such as HPLC purification.

The most advanced of this class of polyproteins is termed XTEN (Amunix) and is 864 amino acids long and comprised of six amino acids (A, E, G, P, S and T). Enabled by the biodegradable nature of the polymer, this is much larger than the 40 KDa PEGs typically used and confers a concomitantly greater half-life extension. The fusion of XTEN to protein drugs results in half-life extension by 60- to 130-fold over native molecules. Two fully recombinantly produced XTENylated products have entered the clinic, namely VRS-859 (Exenatide-XTEN) and VRS-317 (human growth hormone-XTEN). In Phase 1a studies, VRS-859 was found to be well-tolerated and efficacious in patients with Type 2 diabetes. VRS-317 reported superior pharmacokinetic and pharmacodynamic properties compared with previously studied rhGH products and has the potential for once-monthly dosing. A second polymer based on similar conceptual considerations is PAS (XL-Protein GmbH)9. A random coil polymer comprised of an even more restricted set of only three small uncharged amino acids, proline, alanine and serine. Whether differences in the biophysical properties of PAS and the highly negatively charged XTEN may contribute to differences in biodistribution and/or in vivo activity is yet unknown but will be revealed as these polyproteins are incorporated into more therapeutics and the behaviour of the fusions characterised.

All the protein-protein fusions, whether the partner is Fc, HSA, XTEN or PAS, are genetically encoded and consequently suffer from similar constraints. One limitation is that only naturally occurring amino acids are incorporated, unlike the methods employing chemical conjugation which allow the use of synthetic proteins incorporating non-natural amino acids. Although methods to overcome this by expanding the genetic code are being developed by companies such as Ambrx or Sutro, they are not yet in wide use. A second limitation is that either the N- or C-terminus of the protein needs to be fused to the partner. Oftentimes, the protein termini are involved in receptor interactions and genetic fusion to one or both termini can greatly impair activity. Since the site of PEG or lipid conjugation can be anywhere on the protein, it can be optimised to maximise biological activity of the resulting therapeutic.

Hybrid Methods Merging Synthetic Proteins with Half-Life Extension Proteins

While genetic fusions have historically offered the potential for greater half-life extension, they lack the advantages afforded by the methods utilising chemical conjugation, PEGylation and lipidation, in terms of flexibility of attachment sites and incorporation of unnatural amino acids or modifications to the protein backbone. One of the first efforts to merge the advantages of the genetic fusions with chemical conjugation for half-life extension was carried out by researchers at the Scripps Research Institute in La Jolla with the technology which later formed the basis for the biotech company CovX. Using a catalytic aldolase antibody, these researchers developed a platform through which the active site lysine of the antibody forms a reversible covalent enamine bond with a beta-diketone incorporated into a protein or small molecule. The resulting complex is termed a CovXBody™. This approach combines the functional qualities of a protein drug or small molecule with the long serum half-life of an antibody, not through a genetic fusion but rather through a chemical linkage. Following the initial demonstration of the technology, researchers expanded upon the use of CovX-Body™ prototype that is based on an integrin targeting peptidomimetic pharmacophore. At least three molecules based on this architecture have entered clinical development: CVX-096, a Glp-1R agonist; CVX-060, an Angiopoietin-2 binding protein; and CVX-045, a thrombospondin mimetic.

Recently, the XTEN polyprotein has also been used in a chemical conjugation model2 making it even more directly analogous to PEG. The first example of an XTENylated protein that was created using this method is GLP2-2G-XTEN in which the protein is chemically conjugated to the XTEN protein polymer using maleimide-thiol chemistry. The chemically conjugated GLP2-2GXTEN molecules exhibited comparable in vitro activity, in vitro plasma stability and pharmacokinetics in rats comparable to recombinantly-fused GLP2-2G-XTEN.

The number and spacing of reactive groups such as lysine or cysteine side chains in the completely designed sequences of XTEN or PAS polyproteins can be precisely controlled through site-directed changes due to the restricted amino acid sets from which they are composed. This provides an additional degree of flexibility over methods which might utilise Fc or albumin whose sequences naturally contain many reactive groups and stands in contrast to the CovX technology which relies on a reactive residue in a highly specialised active site. In addition, the lack of tertiary structure of XTEN or PAS should provide more flexibility over the conditions and chemistries used in coupling and in the purification of conjugates.

In summary, hybrid protein half-life extension methods are emerging that combine the advantages and overcome the individual limitations of chemical conjugation and genetic fusions methods. These methods enable the creation of molecules based on recombinant polyprotein-based partners that impart longer half-life but free the therapeutic protein moieties from the limitations of being composed solely of natural L-amino acids or configured solely as linear, unidirectional polyproteins fused at either the N- or C-terminus, thus opening the door to a wide range of longer acting protein based drugs.

Exemplary Dosages and Administration Strategies

As described above, compositions of the invention may include a "therapeutically effective amount" or a "prophylactically effective amount" of a protein of the invention (or first and second amounts in the case of a combination composition comprising a protein of the invention and a second component; first, second, and third amounts in the case of a combination composition comprising two proteins of invention and a secondary agent or a protein of the invention and two secondary agents; etc.). To better illustrate particular aspects, a detailed discussion of dosage principles is further provided here.

In practicing the invention, the amount or dosage range of the protein employed typically is one that effectively induces, promotes, or enhances epithelialisation of a wound (in the context of wound treatment), or the amount or dosage range of the protein employed typically is one that effectively modifies the gene expression profile of cells of the nervous system to slow progression of a neurodegenerative condition, or the amount or dosage range of the protein employed typically is one that modifies the gene expression profile of cells in the context of treating a tissue degenerative condition in an equine mammal. In still another aspect, a daily dosage of active ingredient (e.g., protein of the invention) of about 0.01 to 100 milligrams per kilogram of body weight is provided to a patient.

Ordinarily, about 1 to about 5 or about 1 to about 10 milligrams per kilogram per day given in divided doses of about 1 to about 6 times a day or in sustained release form may be effective to obtain desired results. In one embodiment, the dosage is 10-100, 30-70, 40-60 and ideally about 50 µg/ml.

As a non-limiting example, treatment of disease in humans or animals can be provided by administration of a daily dosage of protein of the invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every about 24, 12, 8, 6, 4, or 2 hours, or any combination thereof.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1 pTT3 Expression Vector Construction

All vectors comprise the relevant PSG1 or CC49 open reading frame (ORF) subcloned into the pTT3 expression vector in-frame with a carboxy terminus V5-His tag obtained from the pBlueBac4.5-V5-His vector. Vectors expressing full-length PSG1 were described previously. (Shanley et al., 2013; Houston et al., 2016). CC49 sequences were obtained by PCR and directionally subcloned into pTT3 using PCR primers containing EcoRI and HindIII restriction sites. The previously engineered V5-His tag was removed using site directed mutagenesis.

Fc Tag Cloning

Human Fc tag was PCR amplified from samples of Epstein-Barr Virus (EBV) transformed lymphocyte cDNA. The horse Fc tag was amplified from pcDNA-IGHG1 vector gifted by Bettina Wagner. Both human and horse Fc tags were sublcloned into pTT3 vector using HindIII sites engineered into the primer tails and inserted inframe at the 3' end of the ORF of PSG1/CC49. Once the Fc tag was inserted, the internal HindIII site was removed using site directed mutagenesis, to allow in frame transcription of the PSG1 or CC49 ORF with the Fc tag.

Modifications to human Fc tag (the triple substitution YTE (M252Y/S254T/T256E) in the CH2 domain and (H433K/N434F) in the CH3 domain to increase stability and half-life were performed using site directed mutagenesis (see Rath et al, 2015, for Fc modifications https://doi.org/10.3109/07388551.2013.834293). Modifications to Human Fc tag were performed using Site directed mutagenesis (Phusion Site-Directed Mutagenesis Kit-Thermo Fisher Scientific).

Example 2

Figure 1B:
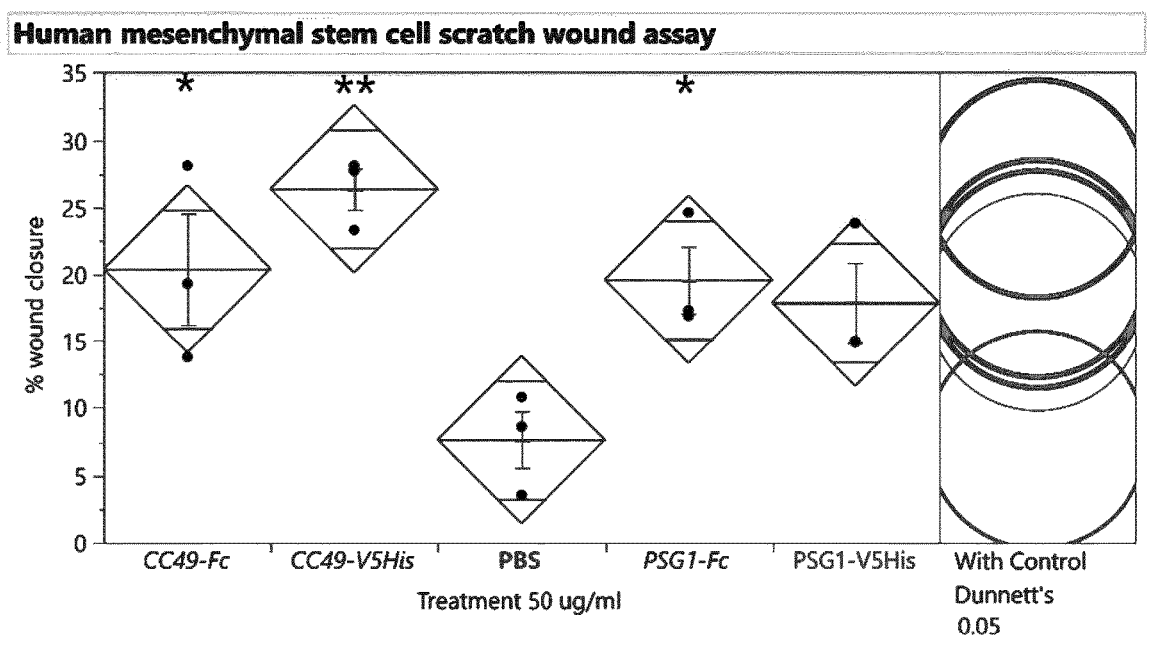
Figures 1C, 1D:
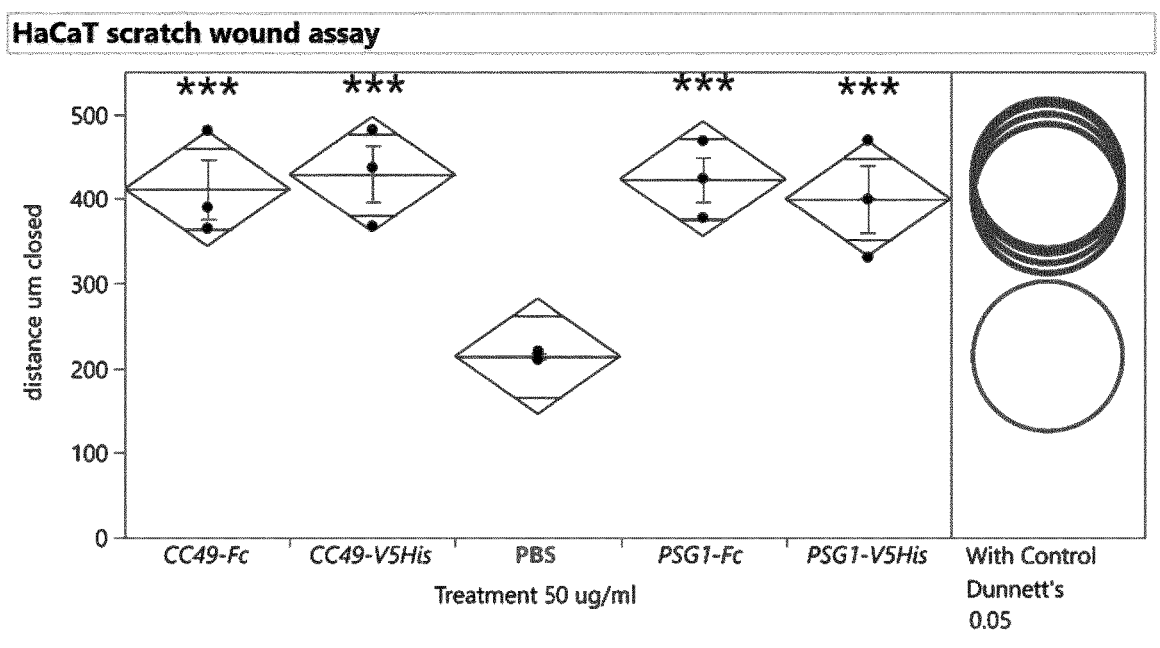

Human immortalised keratinocyte cell line (HaCaT; Boukamp et al., 1988) was purchased from the German Cancer Research Center (DKFZ). Cells were grown in DMEM (D6429, Sigma-Aldrich, UK), supplemented with 10% FBS; 100 µg/ml streptomycin; 100 U/ml penicillin; 2 mM L-Glutamine; and cultured at 37° C. with 5% $CO_2$. Human mesenchymal stem cells (MSC) were grown in MEM (M2279, Sigma-Aldrich, UK), supplemented with 10% FBS; 100 µg/ml streptomycin; 100 U/ml penicillin; 1 ng/ml FGF2 (SRP4037, Sigma-Aldrich, UK) and cultured at 37° C. with 5% $CO_2$. Equine MSC were grown in DMEM (D6429, Sigma-Aldrich, UK), supplemented with 10% FBS; 100 µg/ml streptomycin; 100 U/ml penicillin; 2 mM L-Glutamine; and cultured at 37° C. with 5% $CO_2$. HaCaT ($1\times10^5$ cells/ml) and human or equine MSC ($2\times10^5$ cells/ml) cells were seeded in 1 ml in 6-well plates, with one IBIDI Culture Insert per well. After 24 h, inserts and medium were removed and each well was treated with 1 ml of cell culture medium, supplemented with 50 µg of PSG1-Fc, PSG1-V5His, CC49-Fc, CC49-V5His or 50 µl PBS. Scratch wounds were imaged 16 h post-treatment using an EVOS FL Auto and Wimasis WimScratch analysis or ImageJ analysis was used to determine degree of wound closure. We determined that PSG1 or CC49 enhances migration of cell types associated with wound healing, using the human HaCaT keratinocyte cell line and human and equine mesenchymal stem cells (MSC). Results are shown in FIGS. 1A-C.

Example 3

Effect of PSG1 on Wound Closure in Pigs

Figure 2A:
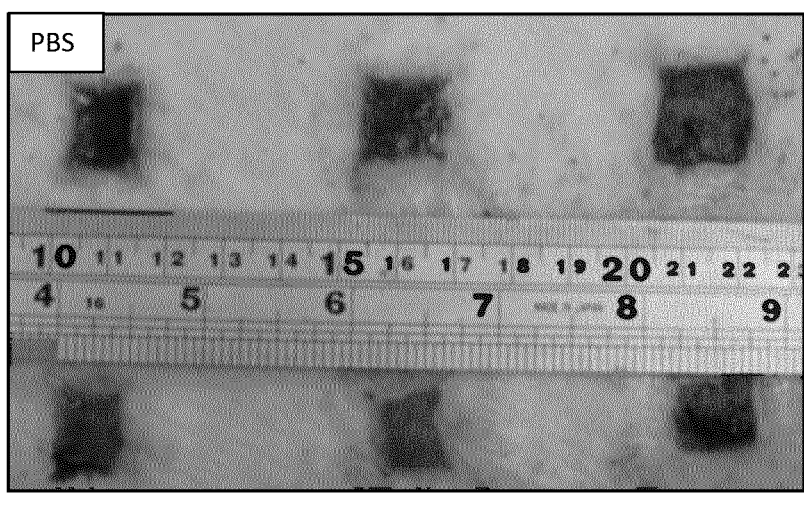
FIGS. 2. A) & B) PSG1 enhances epithelialization of pig skin wounds compared to control group. C) & D) PSG1 enhances closure of mouse skin wounds compared to control group. Similar results were obtained in normal and in diabetic mice.
Figure 2A:
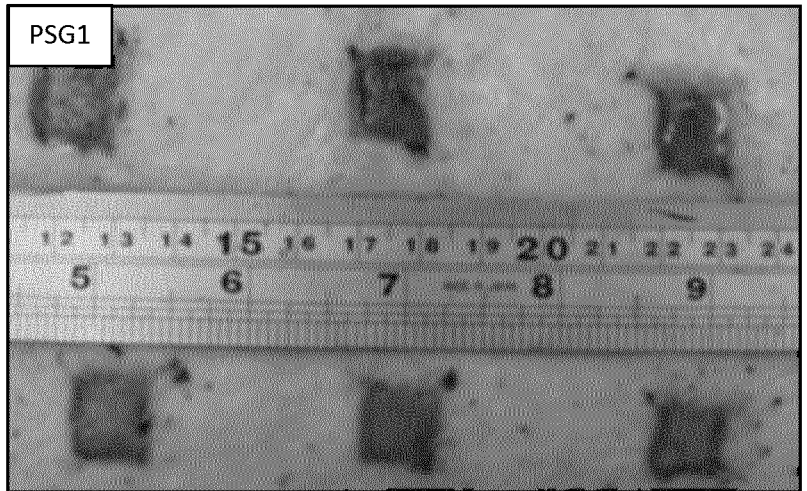
Figure 2B:
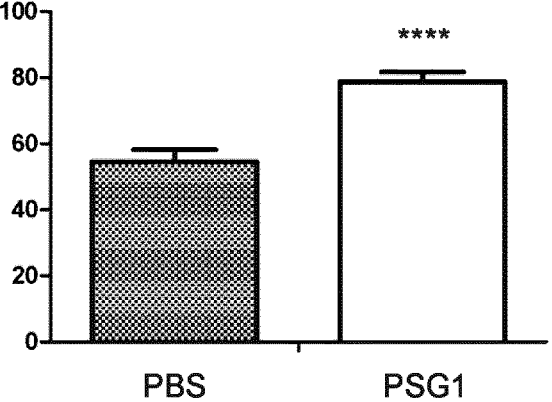

Six 2×2 cm (4 $cm^2$) full thickness excisional wounds were created on each flank of 5 pigs, and treated on day 0 with 1 ml PBS or 250 µg PSG1 in PBS by intradermal injection at eight sites around the wound margin, with a repeated treatment on Day 3. Dressings were changed on days 3 and 7, and wounds were photographed on days 0, 3, 7, and 10, and sampled on day 10. Representative pictures are shown in FIG. 2A. Degree of wound epithelialisation on day 10 is shown in FIG. 2B.

Example 4

Effect of PSG1 on Wound Closure in Mice

Figure 2C:
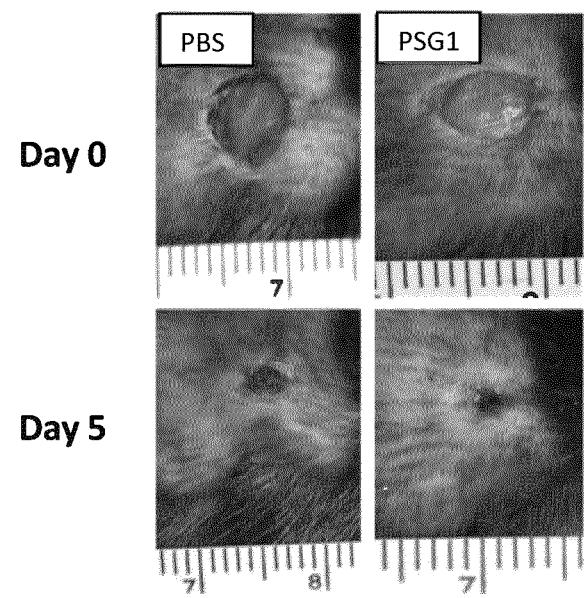
Figure 2D:
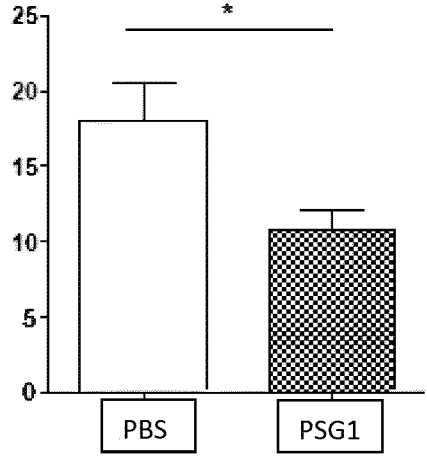

A 0.4 cm diameter circular full thickness excision wound was created in adult male mice of the C57Bl/6J strain and either 100 ul PBS or 50 ug PSG1 in 100 ul PBS was injected intradermally at four equidistant sites around the wound margin. A preliminary dose-response experiment indicated that the lowest active dose of PSG1 achieving maximum wound closure was 50 ug and this dose was used in subsequent experiments. Wounds were measured and photographed immediately following PSG1 administration (day 1) and on day 5 post-wounding. Results are shown in FIGS. 2C and 2D (% wound unhealed day 5).

Example 5

Effect of PSG1 on Gene Expression in the HaCaT Human Cell Line

The HaCaT human keratinocyte cell line was treated in vitro with PSG1 and a Qiagen Wound Healing Profiler qRT-PCR array was used to analyse gene expression changes. Cells were seeded at $1\times10^5$ cells/ml density with 50 ug/ml PSG1 for 24 hrs in 6 well plates and cDNA was prepared and analysed at 24 hours post-treatment. Results of two replicated experiments are shown in FIG. 1D.

Example 6

Mouse Model of Osteoarthritis

A mouse model of osteoarthritis is generated according to the method of Farrell et al. (Farrell E, Fahy N, Ryan A E, Flatharta C O, O'Flynn L, Ritter T, Murphy J M. vIL-10-overexpressing human MSCs modulate naïve and activated T lymphocytes following induction of collagenase-induced osteoarthritis. Stem Cell Res Ther. 2016 May 18; 7(1):74. doi: 10.1186/s13287-016-0331-2. PMID: 27194025).

Protocol for Intra-Articular Injection of Collagenase into the Knee Joint (CIOA Model)

1. Up to nine adult male and nine adult female mice of the C57Bl/6 strain per treatment group are anaesthetized with isoflurane.
2. Hind limbs are shaved and a depilating cream is applied to ensure all hair is removed.
3. The injection area is disinfected with iodine solution.
4. Using a 10 μl Hamilton syringe with a 27G needle, 7 μl of collagenase, phosphate-buffered saline (PBS), or PSG protein in PBS (100 ug/ml), is aspirated into the syringe.
5. The knee is bent slightly and the intra-articular space is located by palpation.
6. The needle is inserted laterally so as not to damage the patellar ligament.
7. The needle is pointed upwards, entering the knee cap and touching the femoral condyle, to avoid piercing the rear of the synovial capsule.
8. Once inside the synovial space, the plunger is slowly pushed to administer the fluid.

9. The needle is retracted and the hind limb is moved gently to facilitate distribution of the fluid.
10. After the procedure, the animals are kept on a heated pad and monitored until fully mobile and recovered from anaesthesia.

Figure 3A:
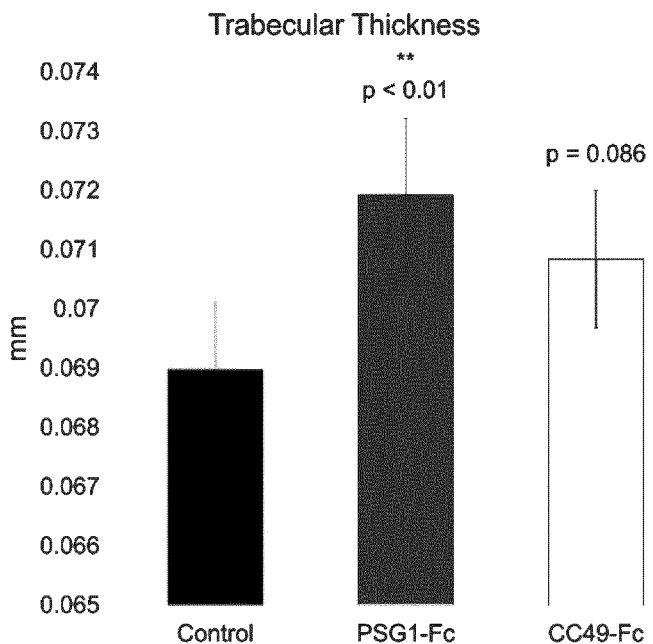
FIG. 3. PSG1-Fc and CC49-Fc reduces osteoarthritis in a mouse collagenase-induced osteoarthritis (CIOA) model. A) PSG1-Fc and CC49-Fc increases bone trabecular thickness in treated groups compared to PBS treated (control) groups. B) PSG1-Fc and CC49-Fc increases mineral density in treated groups when compared to PBS treated groups. C) PSG1-Fc and CC49-Fc reduces osteophyte density in treated groups compared with PBS treated groups.
Figure 3B:
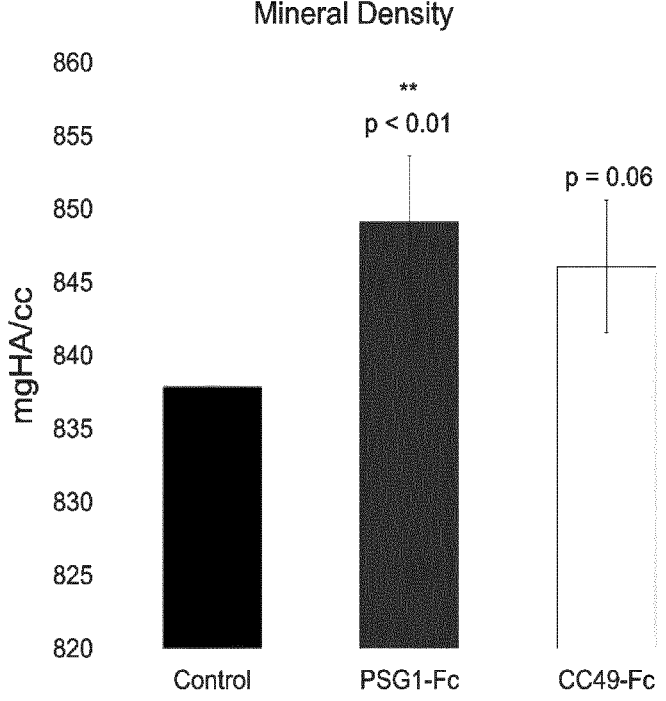
Figure 3C:
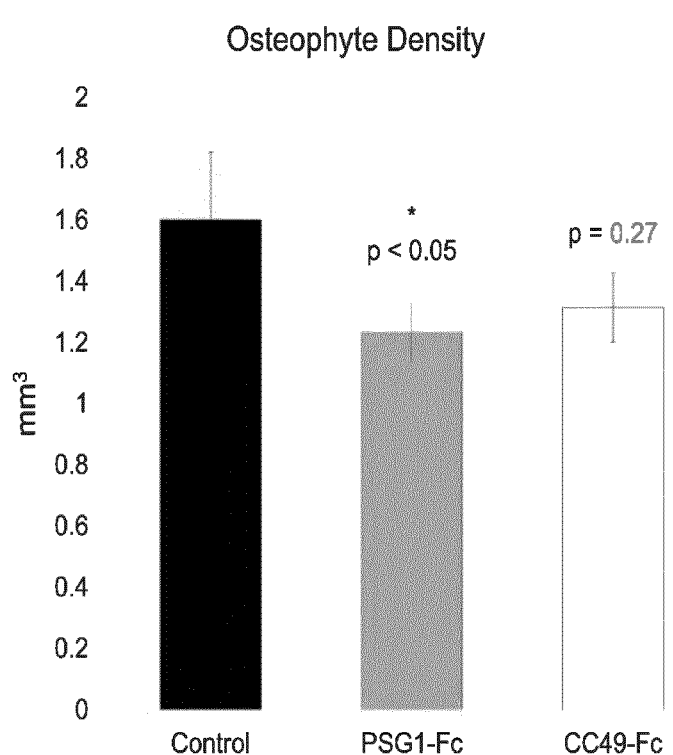

Timeline of experimental protocol (days):
D-7: receipt of mice and one week acclimation
D0: first collagenase injection into knee
D1: second collagenase injection into knee
D7: PBS or PSG1-Fc or CC49-Fc injection into knee (up to 18 mice per treatment)
D42: euthanasia and necropsy At necropsy, both knee joints (untreated and treated) are collected for histological analysis, and blood samples are collected for flow cytometry and cytokine ELISA assays to identify systemic changes to immune cell populations. Experimental outcome measures are primarily focused on the histology of treated joints, using semi-quantitative scoring systems to assess cartilage metrics, synovial thickening, and ectopic bone formation. A subsidiary set of analyses involves flow cytometry to examine immune cell profiles and ELISA of a panel of cytokines in blood and lymph nodes. Results are shown in FIGS. 3A-C and demonstrate the effective treatment of osteoarthritis using PSG1-Fc and CC49-Fc.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of treatment of osteoarthritis or damaged cartilage in a human comprising administering a therapeutically effective amount of Pregnancy-specific glycoprotein 1 (PSG1) to the human, by intra-articular injection.

2. The method of claim 1, in which the PSG1 is Fc-tagged PSG1 (PSG1-Fc).

3. The method of claim 1, in which a PSG1 or PSG1-Fc expression vector is administered to the human.

4. A method of treatment of osteoarthritis or damaged cartilage in an equine mammal comprising administering a therapeutically effective amount of CC49 to the equine mammal by intra-articular injection.

5. The method of claim 4, in which the CC49 is Fc-tagged CC49 (CC49-Fc), and in which the Fc tag is optionally an equine Fc tag.

6. The method of claim 4, in which a CC49 or CC49-Fc expression vector is administered to the equine mammal.

* * * * *

SEQUENCE LISTING

<160> NUMBER OF SEQ ID NOS: 6

<210> SEQ ID NO 1
<211> LENGTH: 419
<212> TYPE: PRT
<213> ORGANISM: Homo sapiens

<400> SEQUENCE: 1

```
Met Gly Thr Leu Ser Ala Pro Pro Cys Thr Gln Arg Ile Lys Trp Lys
1               5                   10                  15

Gly Leu Leu Leu Thr Ala Ser Leu Leu Asn Phe Trp Asn Leu Pro Thr
            20                  25                  30

Thr Ala Gln Val Thr Ile Glu Ala Glu Pro Thr Lys Val Ser Glu Gly
        35                  40                  45

Lys Asp Val Leu Leu Leu Val His Asn Leu Pro Gln Asn Leu Thr Gly
    50                  55                  60

Tyr Ile Trp Tyr Lys Gly Gln Met Arg Asp Leu Tyr His Tyr Ile Thr
65                  70                  75                  80

Ser Tyr Val Val Asp Gly Glu Ile Ile Ile Tyr Gly Pro Ala Tyr Ser
                85                  90                  95

Gly Arg Glu Thr Ala Tyr Ser Asn Ala Ser Leu Leu Ile Gln Asn Val
            100                 105                 110

Thr Arg Glu Asp Ala Gly Ser Tyr Thr Leu His Ile Ile Lys Gly Asp
            115                 120                 125
```

-continued

```
Asp Gly Thr Arg Gly Val Thr Gly Arg Phe Thr Phe Thr Leu His Leu
    130                 135                 140

Glu Thr Pro Lys Pro Ser Ile Ser Ser Ser Asn Leu Asn Pro Arg Glu
145                 150                 155                 160

Thr Met Glu Ala Val Ser Leu Thr Cys Asp Pro Glu Thr Pro Asp Ala
                165                 170                 175

Ser Tyr Leu Trp Trp Met Asn Gly Gln Ser Leu Pro Met Thr His Ser
                180                 185                 190

Leu Lys Leu Ser Glu Thr Asn Arg Thr Leu Phe Leu Leu Gly Val Thr
                195                 200                 205

Lys Tyr Thr Ala Gly Pro Tyr Glu Cys Glu Ile Arg Asn Pro Val Ser
    210                 215                 220

Ala Ser Arg Ser Asp Pro Val Thr Leu Asn Leu Leu Pro Lys Leu Pro
225                 230                 235                 240

Lys Pro Tyr Ile Thr Ile Asn Asn Leu Asn Pro Arg Glu Asn Lys Asp
                245                 250                 255

Val Leu Asn Phe Thr Cys Glu Pro Lys Ser Glu Asn Tyr Thr Tyr Ile
                260                 265                 270

Trp Trp Leu Asn Gly Gln Ser Leu Pro Val Ser Pro Arg Val Lys Arg
                275                 280                 285

Pro Ile Glu Asn Arg Ile Leu Ile Leu Pro Ser Val Thr Arg Asn Glu
    290                 295                 300

Thr Gly Pro Tyr Gln Cys Glu Ile Arg Asp Arg Tyr Gly Gly Ile Arg
305                 310                 315                 320

Ser Asp Pro Val Thr Leu Asn Val Leu Tyr Gly Pro Asp Leu Pro Arg
                325                 330                 335

Ile Tyr Pro Ser Phe Thr Tyr Tyr Arg Ser Gly Glu Val Leu Tyr Leu
                340                 345                 350

Ser Cys Ser Ala Asp Ser Asn Pro Pro Ala Gln Tyr Ser Trp Thr Ile
                355                 360                 365

Asn Glu Lys Phe Gln Leu Pro Gly Gln Lys Leu Phe Ile Arg His Ile
    370                 375                 380

Thr Thr Lys His Ser Gly Leu Tyr Val Cys Ser Val Arg Asn Ser Ala
385                 390                 395                 400

Thr Gly Lys Glu Ser Ser Lys Ser Met Thr Val Glu Val Ser Asp Trp
                405                 410                 415

Thr Val Pro
```

<210> SEQ ID NO 2
<211> LENGTH: 1956
<212> TYPE: DNA
<213> ORGANISM: Artificial Sequence
<220> FEATURE:
<223> OTHER INFORMATION: PSG1-Fc ORF

<400> SEQUENCE: 2

```
atgggaaccc tctcagcccc tccctgcaca cagcgcatca aatggaaggg gctcctgctc      60
acagcatcac ttttaaactt ctggaacctg cccaccactg cccaagtcac gattgaagcc     120
gagccaacca aagtttccga ggggaaggat gttcttctac ttgtccacaa tttgccccag     180
aatcttaccg gctacatctg gtacaaaggg caaatgaggg acctctacca ttacattaca     240
tcatatgtag tagacggtga ataattata tatgggcctg catatagtgg acgagaaaca     300
gcatattcca atgcatccct gctgatccag aatgtcaccc gggaggacgc aggatcctac     360
accttacaca tcataaaggg agatgatggg actagaggag taactggacg tttcaccttc     420
```

-continued

```
accttacacc tggagactcc taagccctcc atctccagca gcaacttaaa tcccagggag      480
accatggagg ctgtgagctt aacctgtgac cctgagactc cagacgcaag ctacctgtgg      540
tggatgaatg gtcagagcct ccctatgact cacagcttga agctgtccga aaccaacagg      600
accctctttc tattgggtgt cacaaagtat actgcaggac cctatgaatg tgaaatacgg      660
aacccagtga gtgccagccg cagtgaccca gtcaccctga atctcctccc gaagctgccc      720
aagccctaca tcaccatcaa caacttaaac cccagggaga taaggatgt cttaaacttc       780 acctgtgaac ctaagagtga gaactacacc tacatttggt ggctaaatgg tcagagcctc      840
ccggtcagtc ccagggtaaa gcgacccatt gaaaacagga tcctcattct acccagtgtc      900
acgagaaatg aaacaggacc ctatcaatgt gaaatacggg accgatatgg tggcatccgc      960
agtgacccag tcaccctgaa tgtcctctat ggtccagacc tccccagaat ttacccttca      1020
ttcacctatt accgttcagg agaagtcctc tacttgtcct gttctgcgga ctctaaccca      1080
ccggcacagt attcttggac aattaatgaa aagtttcagc taccaggaca aaagctcttt      1140
atccgccata ttactacaaa gcatagcggg ctctatgttt gctctgttcg taactcagcc      1200
actggcaagg aaagctccaa atccatgaca gtcgaagtct ctgactggac agttcccgag      1260
cccaaatctt gtgacaaaac tcacacatgc ccaccgtgcc cagcacctga actcctgggg      1320
ggaccgtcag tcttcctctt ccccccaaaa cccaaggaca ccctctacat cacccgggaa      1380
cctgaggtca catgcgtggt ggtggacgtg agccacgaag accctgaggt caagttcaac      1440
tggtacgtgg acggcgtgga ggtgcataat gccaagacaa agccgcggga ggagcagtac      1500
aacagcacgt accgtgtggt cagcgtcctc accgtcctgc accaggactg gctgaatggc      1560
aaggagtaca agtgcaaggt ctccaacaaa gccctcccag cccccatcga gaaaaccatc      1620
tccaaagcca aagggcagcc ccgagaacca caggtgtaca ccctgccccc atcccgggat      1680
gagctgacca gaaccaggt cagcctgacc tgcctggtca aaggcttcta tcccagcgac      1740
atcgccgtgg agtgggagag caatgggcag ccggagaaca actacaagac cacgcctccc      1800
gtgctggact ccgacggctc cttcttcctc tacagcaagc tcaccgtgga caagagcagg      1860
tggcagcagg ggaacgtctt ctcatgctcc gtgatgcatg aggctctgca gttccactac      1920
acgcagaaga gcctctccct gtctccgggt aaatga                               1956
```

<210> SEQ ID NO 3
<211> LENGTH: 699
<212> TYPE: DNA
<213> ORGANISM: Artificial Sequence
<220> FEATURE:
<223> OTHER INFORMATION: Modified human Fc ORF

<400> SEQUENCE: 3

```
gagcccaaat cttgtgacaa aactcacaca tgcccaccgt gcccagcacc tgaactcctg       60 ggggaccgt cagtcttcct cttcccccca aaacccaagg acaccctcta catcacccgg       120
gaacctgagg tcacatgcgt ggtggtggac gtgagccacg aagaccctga ggtcaagttc      180
aactggtacg tggacggcgt ggaggtgcat aatgccaaga caaagccgcg gggaggagcag     240 tacaacagca cgtaccgtgt ggtcagcgtc ctcaccgtcc tgcaccagga ctggctgaat      300
ggcaaggagt acaagtgcaa ggtctccaac aaagccctcc agcccccat cgagaaaacc       360 atctccaaag ccaaagggca gccccgagaa ccacaggtgt acaccctgcc cccatcccgg      420
gatgagctga ccaagaacca ggtcagcctg acctgcctgg tcaaaggctt ctatcccagc      480
```

```
gacatcgccg tggagtggga gagcaatggg cagccggaga acaactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gaagttccac     660
tacacgcaga agagcctctc cctgtctccg ggtaaatga                           699
```

```
<210> SEQ ID NO 4
<211> LENGTH: 162
<212> TYPE: PRT
<213> ORGANISM: Equus caballus

<400> SEQUENCE: 4

Met Gln Ser Pro Ser Gly Pro Ala His Arg Gly Cys Val Pro Trp Gln
1               5                   10                  15

Ala Leu Leu Leu Ala Val Ser Ile Leu Ala Phe Trp Asn Leu Pro Ala
            20                  25                  30

Thr Val Gln Phe Thr Ile Glu Ser Val Pro Asn Asn Val Thr Glu Gly
        35                  40                  45

Lys Asp Val Leu Leu Leu Val His Asn Leu Thr Gly Asn Ile Leu Gly
    50                  55                  60

Tyr Met Trp Phe Lys Gly Asn Gly Ala Arg Pro His Lys Gln Ile Lys
65                  70                  75                  80

Phe Tyr Asp Val Asp Thr Lys Ala Phe Ser Thr Gly Pro Leu Ala Thr
            85                  90                  95

Gly Arg Glu Thr Met Tyr Pro Asn Gly Ser Leu Leu Phe Gln Asn Val
            100                 105                 110

Thr Thr Glu Tyr Ala Gly Asn Tyr Thr Leu Leu Val Leu Lys Arg Ser
        115                 120                 125

Leu Ile Tyr Glu Val Gly Thr Gly Gln Val His Val Tyr Asn Pro Gly
    130                 135                 140

Ser Asn Thr Ser Ile Gly Ile Ser Val Ile His Lys Asp Pro Ser Tyr
145                 150                 155                 160

Arg Ala
```

```
<210> SEQ ID NO 5
<211> LENGTH: 1206
<212> TYPE: DNA
<213> ORGANISM: Artificial Sequence
<220> FEATURE:
<223> OTHER INFORMATION: CC49-Fc ORF

<400> SEQUENCE: 5
atgcaatcac cctcaggccc tgctcacaga ggatgtgtcc cttggcaggc gctcctcttg      60
gcagtctcaa tcttagcctt ctggaacctg cccgccactg tccagttcac tattgagtcg     120
gtgccgaaca atgttactga aggaaaggat gttcttctac ttgtccacaa tctgactggg     180
aatattctag ctatatgtg gttcaaaggg aatggagcac gtccacataa acaaattaag     240
ttttatgatg tagacacaaa agcattttcc acaggggcct cagccacagg tcgagagaca     300
atgtacccca atggatccct gctgttccag aatgtcacga cggagtacgc aggaaactac     360
acactacttg tcctaaaaag atccttgata tatgaagtag gaactggaca agtccatgta     420
tacaatccag ggtcaaatac ctccattgga ataactgtaa tacataaaga ccccagttac     480
agagccgagc ccattcccga caaccaccaa aaagtgtgcg acatgagcaa gtgtcccaaa     540
tgcccagctc ctgagctcct gggagggcct cggtcttca tcttcccccc gaatcccaag     600
gacaccctca tgatcacccg aacacccgag gtcacctgcg tggtggtgga tgtgagccag     660
```

-continued

```
gagaaccctg atgtcaagtt caactggtac atggacgggg tggaggtgcg cacagccacg    720
acgaggccga aggaggagca gttcaacagc acttaccgcg tggtcagcgt cctccgcatc    780
cagcaccagg actggctgtc aggaaaggag ttcaagtgta aggtcaacaa ccaagccctc    840
ccacaaccca tcgagaggac catcaccaag accaaagggc ggtcccagga gccgcaagtg    900
tacgtcctgg ccccacaccc agacgagctg tccaagagca aggtcagcgt gacctgcctg    960
gtcaaggact tctacccacc tgaaatcaac atcgagtggc agagtaatgg gcagccagag   1020
ctggagacca agtacagcac cacccaagcc cagcaggaca gcgacgggtc ctacttcctg   1080
tacagcaagc tctccgtgga caggaacagg tggcagcagg aacgacatt cacgtgtggg     1140 gtgatgcacg aggctctcca caatcactac acacagaaga acgtctccaa gaacccgggt   1200
aaatga                                                             1206

<210> SEQ ID NO 6
<211> LENGTH: 1206
<212> TYPE: DNA
<213> ORGANISM: Artificial Sequence
<220> FEATURE:
<223> OTHER INFORMATION: Equine Fc ORF

<400> SEQUENCE: 6
atgcaatcac cctcaggccc tgctcacaga ggatgtgtcc cttggcaggc gctcctcttg     60
gcagtctcaa tcttagcctt ctggaacctg cccgccactg tccagttcac tattgagtcg    120
gtgccgaaca atgttactga aggaaaggat gttcttctac ttgtccacaa tctgactggg    180
aatattctag gctatatgtg gttcaaaggg aatggagcac gtccacataa acaaattaag    240
ttttatgatg tagacacaaa agcattttcc acagggcctc tagccacagg tcgagagaca    300
atgtacccca atggatccct gctgttccag aatgtcacga cggagtacgc aggaaactac    360
acactacttg tcctaaaaag atccttgata tatgaagtag aactggaca agtccatgta     420 tacaatccag ggtcaaatac ctccattgga ataactgtaa tacataaaga ccccagttac    480
agagccgagc ccattcccga caaccaccaa aaagtgtgcg acatgagcaa gtgtcccaaa    540
tgcccagctc ctgagctcct gggagggcct tcggtcttca tcttcccccc gaatcccaag    600
gacaccctca tgatcacccg aacacccgag gtcacctgcg tggtggtgga tgtgagccag    660
gagaaccctg atgtcaagtt caactggtac atggacgggg tggaggtgcg cacagccacg    720
acgaggccga aggaggagca gttcaacagc acttaccgcg tggtcagcgt cctccgcatc    780
cagcaccagg actggctgtc aggaaaggag ttcaagtgta aggtcaacaa ccaagccctc    840
ccacaaccca tcgagaggac catcaccaag accaaagggc ggtcccagga gccgcaagtg    900
tacgtcctgg ccccacaccc agacgagctg tccaagagca aggtcagcgt gacctgcctg    960
gtcaaggact tctacccacc tgaaatcaac atcgagtggc agagtaatgg gcagccagag   1020
ctggagacca agtacagcac cacccaagcc cagcaggaca gcgacgggtc ctacttcctg   1080
tacagcaagc tctccgtgga caggaacagg tggcagcagg aacgacatt cacgtgtggg     1140 gtgatgcacg aggctctcca caatcactac acacagaaga acgtctccaa gaacccgggt   1200
aaatga                                                             1206
```